US006834239B2

(12) United States Patent
Lobanov et al.

(10) Patent No.: US 6,834,239 B2
(45) Date of Patent: Dec. 21, 2004

(54) METHOD, SYSTEM, AND COMPUTER PROGRAM PRODUCT FOR DETERMINING PROPERTIES OF COMBINATORIAL LIBRARY PRODUCTS FROM FEATURES OF LIBRARY BUILDING BLOCKS

(76) Inventors: Victor S. Lobanov, 1002 Darby Dr., Yardley, PA (US) 19067; Dimitris K. Agrafiotis, 660 Perimiter Dr., Downingtown, PA (US) 19335; F. Raymond Salemme, 1970 Timber Lakes Dr., Yardley, PA (US) 19067

( * ) Notice: Subject to any disclaimer, the term of this patent is extended or adjusted under 35 U.S.C. 154(b) by 345 days.

(21) Appl. No.: 09/934,084

(22) Filed: Aug. 22, 2001

(65) Prior Publication Data

US 2002/0029114 A1 Mar. 7, 2002

Related U.S. Application Data

(60) Provisional application No. 60/226,682, filed on Aug. 22, 2000, provisional application No. 60/235,937, filed on Sep. 28, 2000, and provisional application No. 60/274,238, filed on Mar. 9, 2001.

(51) Int. Cl.[7] .............................................. G06F 19/00
(52) U.S. Cl. ........................................ 702/22; 702/19
(58) Field of Search ................................. 702/19, 22

(56) References Cited

U.S. PATENT DOCUMENTS

| 4,773,099 A | 9/1988 | Bokser ........................ 382/14 |
| 4,811,217 A | 3/1989 | Tokizane et al. ............. 364/300 |
| 4,859,736 A | 8/1989 | Rink ........................... 525/54.1 |
| 4,908,773 A | 3/1990 | Pantoliano et al. .......... 364/496 |
| 4,935,875 A | 6/1990 | Shah et al. .................. 364/497 |
| 4,939,666 A | 7/1990 | Hardman .................... 364/496 |
| 5,010,175 A | 4/1991 | Rutter et al. ................ 530/334 |
| 5,025,388 A | 6/1991 | Cramer, III et al. ......... 364/496 |
| 5,095,443 A | 3/1992 | Watanabe .................... 364/513 |
| 5,155,801 A | 10/1992 | Lincoln ........................ 395/22 |
| 5,167,009 A | 11/1992 | Skeirik ........................ 395/27 |

(List continued on next page.)

FOREIGN PATENT DOCUMENTS

| EP | 0 818 744 A2 | 1/1998 | ........... G06F/17/50 |
| WO | WO 93/20242 | 10/1993 | ............ C12Q/1/70 |
| WO | WO 94/28504 A1 | 12/1994 | ........... G06F/15/60 |
| WO | WO 95/01606 | 1/1995 | ........... G06F/15/42 |
| WO | WO 97/27559 | 7/1997 | ........... G06F/19/00 |
| WO | WO 98/20437 A2 | 5/1998 | ........... G06F/17/50 |
| WO | WO 98/20459 | 5/1998 | ........... G06T/11/20 |
| WO | WO 99/35599 A1 | 7/1999 | ........... G06F/17/50 |

OTHER PUBLICATIONS

Linusson et al., "Statistical Molecular Design of Building Blocks for Combinatorial Chemistry," *Journal of Medical Chemistry*. vol. 43, No. 7, American Chemical Society, Published on Web Mar. 8, 2000, pp. 1320–1328.

(List continued on next page.)

*Primary Examiner*—Marianne P. Allen
*Assistant Examiner*—Channing S. Mahatan
(74) *Attorney, Agent, or Firm*—Wilson Sonsini Goodrich & Rosati

(57) ABSTRACT

The present invention determines properties of combinatorial library products from features of library building blocks. At least one feature is determined for each building block of a combinatorial library having a plurality of products. A training subset of products is selected from the products, and at least one property is determined for each product of the training subset. A building block set is identified for each product of the training subset, and an input features vector is formed from the features of the identified building blocks for each product of the training subset. A supervised machine learning approach is used to infer a mapping function that transforms the input features vector for each product of the training subset to the corresponding at least one property for each product of the training subset. After the mapping function is inferred, it is used for determining properties of other products of the library from their corresponding input features vectors.

13 Claims, 21 Drawing Sheets

U.S. PATENT DOCUMENTS

| | | |
|---|---|---|
| 5,181,259 A | 1/1993 | Rorvig .......................... 382/36 |
| 5,240,680 A | 8/1993 | Zuckermann et al. .......... 422/67 |
| 5,260,882 A | 11/1993 | Blanco et al. ................ 364/499 |
| 5,265,030 A | 11/1993 | Skolnick et al. ............. 364/496 |
| 5,270,170 A | 12/1993 | Schatz et al. ............... 435/7.37 |
| 5,288,514 A | 2/1994 | Ellman ........................... 427/2 |
| 5,307,287 A | 4/1994 | Cramer, III et al. ......... 364/496 |
| 5,323,471 A | 6/1994 | Hayashi ........................ 382/15 |
| 5,331,573 A | 7/1994 | Balaji et al. ................. 364/500 |
| 5,434,796 A | 7/1995 | Weininger ................... 364/496 |
| 5,436,850 A | 7/1995 | Eisenberg et al. ........... 364/496 |
| 5,442,122 A | 8/1995 | Noda et al. .................. 564/426 |
| 5,463,564 A | 10/1995 | Agrafiotis et al. ........... 364/496 |
| 5,499,193 A | 3/1996 | Sugawara et al. ........... 364/500 |
| 5,519,635 A | 5/1996 | Miyake et al. ............... 364/497 |
| 5,524,065 A | 6/1996 | Yagasaki ..................... 382/226 |
| 5,526,281 A | 6/1996 | Chapman et al. ............ 364/496 |
| 5,545,568 A | 8/1996 | Ellman ........................ 436/518 |
| 5,549,974 A | 8/1996 | Holmes ....................... 428/403 |
| 5,553,225 A | 9/1996 | Perry .......................... 395/157 |
| 5,565,325 A | 10/1996 | Blake .......................... 435/7.1 |
| 5,574,656 A | 11/1996 | Agrafiotis et al. ........... 364/500 |
| 5,585,277 A | 12/1996 | Bowie et al. ................ 436/518 |
| 5,598,510 A | 1/1997 | Castelaz ....................... 395/23 |
| 5,602,755 A | 2/1997 | Ashe et al. .................. 364/498 |
| 5,602,938 A | 2/1997 | Akiyama et al. ............ 382/155 |
| 5,612,895 A | 3/1997 | Balaji et al. ................. 364/496 |
| 5,621,861 A | 4/1997 | Hayashi et al. ................ 395/23 |
| 5,634,017 A | 5/1997 | Mohanty et al. ............ 395/326 |
| 5,635,598 A | 6/1997 | Lebl et al. ................... 530/334 |
| 5,670,326 A | 9/1997 | Beutel ......................... 435/7.1 |
| 5,679,582 A | 10/1997 | Bowie et al. ................ 435/518 |
| 5,684,711 A | 11/1997 | Agrafiotis et al. ........... 364/500 |
| 5,703,792 A | 12/1997 | Chapman .................... 364/476 |
| 5,712,171 A | 1/1998 | Zambias et al. ............. 436/518 |
| 5,712,564 A | 1/1998 | Hayosh ....................... 324/210 |
| 5,734,796 A | 3/1998 | Pao .............................. 395/22 |
| 5,736,412 A | 4/1998 | Zambias et al. ............. 436/518 |
| 5,740,326 A | 4/1998 | Boulet et al. .................. 395/27 |
| 5,789,160 A | 8/1998 | Eaton et al. .................... 435/6 |
| 5,807,754 A | 9/1998 | Zambias et al. ............. 436/518 |
| 5,811,241 A | 9/1998 | Goodfellow et al. ......... 435/7.1 |
| 5,832,494 A | 11/1998 | Egger et al. ................. 707/102 |
| 5,858,660 A | 1/1999 | Eaton et al. .................... 435/6 |
| 5,861,532 A | 1/1999 | Brown et al. ................ 564/123 |
| 5,866,334 A | 2/1999 | Beutel ............................ 435/6 |
| 5,901,069 A | 5/1999 | Agrafiotis et al. ...... 364/528.03 |
| 5,908,960 A | 6/1999 | Newlander ................... 564/177 |
| 5,933,819 A | 8/1999 | Skolnick et al. ............... 706/21 |
| 6,014,661 A | 1/2000 | Ahlberg et al. ................ 707/3 |
| 6,026,397 A | 2/2000 | Sheppard ....................... 707/5 |
| 6,037,135 A | 3/2000 | Kubo et al. ................ 435/7.24 |
| 6,049,797 A | 4/2000 | Guha et al. ..................... 707/6 |
| 6,185,506 B1 | 2/2001 | Cramer et al. ................ 702/19 |

OTHER PUBLICATIONS

Borg, Ingwer and Groenen, Patrick, *Modern Multidimensional Scaling Theory and Applications,* Springer Series in Statistics, 1997, entire book submitted.

Agrafiotis, D.K. et al., "Advances in diversity profiling and combinatorial series design," *Molecular Diversity,* Kluwer Academic Publishers, vol. 4, 1999, pp. 1–22.

Agrafiotis, D.K. and Lobanov, V.S., "An Efficient Implementation of Distance–Based Diveristy Measures Based on k–d Trees," *Journal of Chemical Information and Computer Science,* American Chemical Society, vol. 39, No. 1, Jan./Feb. 1999, pp. 51–58.

Agrafiotis, D.K. and Lobanov, V.S., "Bridging The Gap Between Diversity And QSAR," *Abstracts of Papers Part 1: 215th ACS National Meeting,* American Chemical Society, Mar. 29–Apr. 2, 1998, p. 181–COMP.

Agrafiotis, D.K. and Jaeger, E.P., "Directed Diversity®: An Operating System For Combinatorial Chemistry," *Abstracts of Papers Part 1: 211th ACS National Meeting,* American Chemical Society, Mar. 24–28, 1996, p. 46–COMP.

Agrafiotis, D.K., "Diversity of Chemical Libraries," *Encyclopedia of Computational Chemistry,* John Wiley & Sons Ltd, vol. 1:A–D, 1998, pp. 742–761.

Agrafiotis, D.K., "On the Use of Information Theory for Assessing Molecular Diversity," *Journal of Chemical Information and Computer Science,* American Chemical Society, vol. 37, No. 3, May/Jun. 1997, pp. 576–580.

Agrafiotis, D.K. et al., "Parallel QSAR," *Abstracts of Papers Part 1: 217th ACS National Meeting,* Mar. 21–25, 1999, p. 50–COMP.

Agrafiotis, D.K. et al., "PRODEN: A New Program for Calculating Integrated Projected Populations," *Journal of Computational Chemistry,* John Wiley & Sons, Inc., vol. 11, No. 9, Oct. 1990, pp. 1101–1110.

Agrafiotis, D.K. and Jaeger, E.P., "Stochastic Algorithms for Exploring Molecular Diversity," *Abstracts of Papers Part 1: 213th ACS National Meeting,* American Chemical Society, Apr. 13–17, 1997, p. 16–CINF.

Agrafiotis, D., "Theoretical Aspects of the Complex: Arts and New Technologies," *Applications and Impacts Information Processing '94,* North–Holland, vol. II, 1994, pp. 714–719.

Biswas, G. et al., "Evaluation of Projection Algorithms," *IEEE Transactions On Pattern Analysis And Machine Intelligence,* IEEE Computer Society, vol. PAMI–3, No. 6, Nov. 1981, pp. 701–708.

Bonchev, D. and Trinajstić, N., "Information theory, distance matrix, and molecular branching," *The Journal of Chemical Physics,* American Institute of Physics, vol. 67, No. 10, Nov. 15, 1977, pp. 4517, 4520–4533.

Chang, C.L. and Lee, R.C.T., "A Heuristic Relaxation Method for Nonlinear Mapping in Cluster Analysis," *IEEE Transactions on Systems, Man, and Cybernetics,* IEEE Systems, Man, and Cybernetics Society, vol. SMC–3, Mar. 1973, pp. 197–200.

Cramer, R.D. et al., "Virtual Compound Libraries: A New Approach to Decision Making in Molecular Discovery Research," *J. Chem. Inf. Comput. Sci.,* American Chemical Society, vol. 38, No. 6, Nov./Dec. 1998, pp. 1010–1023.

DeMers, D. and Cottrell, G., "Non–Linear Dimensionality Reduction," *Advances in Neural Information Processing Systems,* vol. 5, 1993, pp. 580–587.

Frey, P.W. and Slate, D.J., "Letter Recognition Using Holland–Style Adaptive Classifiers," *Machine Learning,* Kluwer Academic Publishers, vol. 6, 1991, pp. 161–182.

Friedman, J.H., "Exploratory Projection Pursuit," *Journal of the American Statistical Association,* American Statistical Association, vol. 82, No. 397, Mar. 1987, pp. 249–266.

Friedman, J.H. and Tukey, J.W., "A Projection Pursuit Algorithm for Exploratory Data Analysis," *IEEE Transactions on Computers,* IEEE Computer Society, vol. C–23, No. 9, Sep. 1974, pp. 881–889.

Garrido, L. et al., "Use of Multilayer Feedforward Neural Nets As A Display Method for Multidimensional Distributions," *International Journal of Neural Systems,* World Scientific Publishing Co. Pte. Ltd., vol. 6, No. 3, Sep. 1995, pp. 273–282.

Ghose, A.K. et al., "Prediction of Hydrophobic (Lipophillic) Properties of Small Organic Molecules Using Fragmental Methods: An Analysis of ALGOP and CLOGP Methods," *Journal of Physical Chemistry,* American Chemical Society, vol. 102, No. 21, May 21, 1998, pp. 3762–3772.

Hall, L.H. and Kier, L.B., "The Molecular Connectivity Chi Indexes and Kappa Shape Indexes in Structure–Property Modeling," *Reviews in Computational Chemistry: Advances,* VCH Publishers, Inc., 1991, pp. 367–422.

Hecht–Nielsen, R., "Replicator Neural Networks for Universal Optimal Source Coding," *Science,* American Association for the Advancement of Science, vol. 269, Sep. 29, 1995, pp. 1860–1863.

Hotelling, H., "Analysis of a Complex of Statistical Variables into Principal Components," *The Journal of Educational Psychology,* Warwick and York, Inc., vol. XXIV, No. 6, Sep. 1933, pp. 417–441.

Hotelling, H., "Analysis of a Complex of Statistical Variables into Principal Components," *The Journal of Educational Psychology,* Warwick and York, Inc., vol. XXIV, No. 7, Oct. 1933, pp. 498–520.

Lee, R.C.T. et al., "A Triangulation Method for the Sequential Mapping of Points from N–Space to Two–Space," *IEEE Transactions on Computers,* The Institute of Electrical and Electronics Engineers, Mar. 1977, pp. 288–292.

Lipinski, C.A. et al., "Experimental and computational approaches to estimate solubility and permeability in drug discovery and development settings," *Advanced Drug Delivery Reviews,* Elsevier Science B.V., vol. 23, 1997, pp. 3–25.

Lobanov, V.S. and Agrafiotis, D.K., "Intelligent Database Mining Techniques," *Abstracts of Papers Part 1: 215th ACS National Meeting,* Mar. 29–Apr. 2, 1998, p. 19–COMP.

Lobanov, V.S. et al., "Rational Selections from Virtual Libraries," *Abstracts of Papers Part 1: 217th ACS National Meeting,* Mar. 21–25, 1999, p. 181–COMP.

Mao, J. and Jain, A.K., "Artificial Neural Networks for Feature Extraction and Multivariate Data Projection," *IEEE Transactions on Neural Networks,* IEEE Neural Networks, vol. 6, No.2, Mar. 1995, pp. 296–317.

Oja, E., "Principal Component, Minor Components, and Linear Neural Networks," *Neural Networks,* Pergamon Press Ltd., vol. 5, 1992, pp. 927–935.

Patterson, D.E. et al., "Neighborhood Behavior: A Useful Concept for Validation of 'Molecular Diversity' Descriptors," *Journal of Medicinal Chemistry,* American Chemical Society, vol. 39, No. 16, 1996, pp. 3049–3059.

Pykett, C.E., "Improving the Efficiency of Sammon's Nonlinear Mapping by Using Clustering Archetypes," *Electronics Letters,* The Institution of Electrical Engineers, vol. 14, No. 25, Dec. 7, 1978, pp. 799–800.

Rubner, J. and Tavan, P., "A Self–Organizing Network for Principal–Component Analysis," *Europhysics Letters,* European Physical Society, vol. 10, No. 7, Dec. 1, 1989, pp. 693–698.

Sadowski, J. et al., "Assessing Similarity and Diversity of Combinatorial Libraries by Spatial Autocorrelation Functions and Neural Networks," *Angewandte Chemie,* VCH, vol. 34, No. 23/24, Jan. 5, 1996, pp. 2674–2677.

Kim, J. et al., "Multiple Neuroal Networks using the Reduced Input Dimension," *Proceedings of the International Conference on Acoustics, Speech, and Signal Processing,* IEEE, vol. 2, Apr. 19–22, 1994, pp. II–601 to II–604.

Barnard, John M. and Downs, Geoff M., "Computer representation and manipulation of combinatorial libraries," *Perspectives in Drug Discovery and Design,* Kluwer Academic Publishers, 1997, pp. 13–30.

Brint, Andrew T. and Willett, Peter, "Upperbound procedures for the identification of similar three–dimensional chemical strucures," *Journal of Computer–Aided Molecular Design,* ESCOM Science Publishers B.V., vol. 2, No. 4, Jan. 1989, pp. 311–320.

Brown, Robert D. and Martin, Yvonne C., "Designing Combinatorial Library Mixtures Using a Genetic Algorithm," *Journal of Medicinal Chemistry,* American Chemical Society, vol. 40, No. 15, 1997, pp. 2304–2313.

Gillet, Valerie J. et al., "The Effectiveness of Reactant Pools for Generating Structurally–Diverse Combinatorial Libraries," *Journal of Chemical and Information Computer Sciences,* American Chemical Society, vol. 37, No. 4, 1997, pp. 731–740.

Gillet, Valerie J. et al., "Selecting Combinatorial Libraries to Optimize Diversity and Physical Properties," *Journal of Chemical Information and Computer Sciences,* American Chemical Society, vol. 39, No. 1, 1999, pp. 169–177.

Kearsley, Simon K. et al., "Chemical Similarity Using Physiochemical Property Descriptors," *Journal of Chemical Information and Computer Sciences,* American Chemical Society, vol. 36, No. 1, 1996, pp. 118–127.

Leland, Burton A. et al., "Managing the Combinatorial Explosion," *Journal of Chemical Information and Computer Sciences,* American Chemical Society, vol. 37, No. 1, 1997, pp. 62–70.

Lewis, Richard A. et al., "Similarity Measures for Rational Set Selection and Analysis of Combinatorial Libraries: The Diverse Property–Derived (DPD) Approach," *Journal of Chemical Information and Computer Sciences,* American Chemical Society, vol. 37, No. 3, 1997, pp. 599–614.

Martin, Eric J. and Critchlow, Roger E., "Beyond Mere Diversity: Tailoring Combinatorial Libraries for Drug Discovery," *Journal of Combinatorial Chemistry,* American Chemical Society, vol. 1, No. 1, 1999, pp. 32–45.

Sheridan, Robert P. et al., "Chemical Similarity Using Geometric Atom Pair Descriptors," *Journal of Chemical Information and Computer Sciences,* American Chemical Society, vol. 36, No. 1, 1996, pp. 128–136.

Willett, Peter et al., "Chemical Similarity Searching," *Journal of Chemical Information and Computer Sciences,* American Chemical Society, vol. 38, No. 6, 1998, pp. 983–996.

Arafiotis, Dimitris K. and Lobanov, Victor S., "Ultrafast Algorithm for Designing Focused Combinational Arrays," *Journal of Chemical Information and Computer Sciences,* American Chemical Society, 2000, vol. 40, No. 4, pp. 1030–1038.

Ajay et al., "Can We Learn To Distinguish between 'Drug–Like' and 'Nondrug–like' Molecules?" *J. Med. Chem.,* 1998, American Chemical Society, vol. 41, No. 18, pp. 3314–3324.

Spellmeyer, D. et al., "Conformational analysis using distance geometry methods," *Journal of Molecular Graphics & Modelling,* Elsevier Science, Inc., vol. 15, No. 1, Feb. 1997, pp. 18–36.

Brown, Robert D. and Martin, Yvonne C., "The Information Content of 2D and 3D Structural Descriptors Relevant to Ligand–Receptor Binding," *Journal of Chemical Information and Computer Sciences,* American Chemical Society, 1997, vol. 37, No. 1, pp. 1–9.

Brown, Robert D. and Martin, Yvonne C., "Use of Structure–Activity Data To Compare Structure–Based Clustering Methods and Descriptors for Use in Compound Selection," *Journal of Chemical Information and Computer Sciences,* American Chemical Society, 1996, vol. 36, No. 3, pp. 572–584.

Cummins, David J. et al., "Molecular Diversity in Chemical Databases: Comparison of Medicinal Chemistry Knowledge Bases and Databases of Commercially Available Compounds," *Journal of Chemical Information and Computer Sciences,* American Chemical Society, 1996, vol. 36, No. 4, pp. 750–763.

Domine, D. et al., "Non–Linear Mapping for Structure–Activity and Structure–Property Modelling," *Journal of Chemometrics,* John Wiley & Sons, Ltd., vol. 7, No. 4, Jul.–Aug. 1993, pp. 227–242.

Saunders, M., "Stochastic Exploration of Molecular Mechanics Energy Surfaces. Hunting for the Global Minimum," *Journal of the American Chemical Society,* American Chemical Society, vol. 109, 10, May 13, 1987, pp. 3150–3152.

Downs, Geoff M. and Barnard, John M., "Techniques for Generating Descriptive Fingerprints in Combinatorial Libraries," *Journal of Chemical Information and Computer Sciences,* American Chemical Society, 1997, vol. 37, No. 1, pp. 59–61.

Gillet, Valerie J., "Background Theory of Molecular Diversity," *Molecular Diversity in Drug Design,* Kluwer Academic Publishers, 1999, pp. 43–65.

Good, Andrew C. and Lewis, Richard A., "New Methodology for Profiling Combinatorial Libraries and Screening Sets: Cleaning Up the Design Process with HARPick," *Journal of Medicinal Chemistry,* American Chemical Society, 1997, vol. 40, No. 24, pp. 3926–3936.

Pal, N.R. and Eluri, V.K., "Two Efficient Connectionist Schemes for Structure Preserving Dimensionality Reduction," *IEEE Transactions on Neural Networks,* IEEE, vol. 9, No. 6, Nov. 1998, pp. 1142–1154.

Jamois, Eric A. et al., "Evaluation of Reagent–Based and Product–Based Strategies in the Design of Combinatorial Library Subsets," *Journal of Chemical Information and Computer Sciences,* American Chemical Society, 2000, vol. 40, No. 1, pp. 63–70.

Kim, H. et al., "Self–Organized Distributed Networks for Learning Highly Nonlinear Mapping," *Intelligent Engineering Systems Through Artificial Neural Networks,* American Society of Mechanical Engineers, vol. 4, Nov. 13–16, 1994, pp. 109–114.

Leach, Andrew R. et al., "Implementation of a System for Reagent Selection and Library Enumeration, Profiling, and Design," *Journal of Chemical Information and Computer Sciences,* American Chemical Society, 1999, vol. 39, No. 6, pp. 1161–1172.

Lobanov, Victor S. and Agrafiotis, Dimitris K., "Stochastic Similarity Selections from Large Combinatorial Libraries," *Journal of Chemical Information and Computer Sciences,* American Chemical Society, Mar./Apr. 2000, vol. 40, No. 2, pp. 460–470.

Matter, Hans and Pötter, Thorsten, "Comparing 3D Pharmacophore Triplets and 2D Fingerprints for Selecting Diverse Compound Subsets," *Journal of Chemical Information and Computer Sciences,* American Chemical Society, 1999, vol. 39, No. 6, pp. 1211–1225.

Matter, Hans, "Selecting Optimally Diverse Compounds from Structure Databases: A Validation Study of Two–Dimensional and Three–Dimensional Molecular Descriptors," *Journal of Medicinal Chemistry,* American Chemical Society, 1997, vol. 40, No. 8, pp. 1219–1229.

Sadowski, Jens and Kubinyi, Hugo, "A Scoring Scheme for Discriminating between Drugs and Nondrugs," *Journal of Medicinal Chemistry,* American Chemical Society, 1998, vol. 41, No. 18, pp. 3325–3329.

Schnur, Dora, "Design and Diversity Analysis of Large Combinatorial Libraries Using Cell–Based Methods," *Journal of Chemical Information and Computer Science,* American Chemical Society, 1999, vol. 39, No. 1, pp. 36–45.

Schuffenhauer, Ansgar et al., "Similarity Searching in Files of Three–Dimensional Chemical Structures: Analysis of the BIOSTER Database Using Two–Dimensional Fingerprints and Molecular Field Descriptors," *Journal of Chemical Information and Computer Science,* American Chemical Society, 2000, vol. 40, No. 2, pp. 295–307.

Turner, David B. et al., "Rapid Quantification of Molecular Diversity for Selective Database Acquisition," *Journal of Chemical Information and Computer Science,* American Chemical Society, 1997, vol. 37, No. 1, pp. 18–22.

Wang, Jing and Ramnarayan, Kal, "Toward Designing Drug–Like Libraries: A Novel Computational Approach for Prediction of Drug Feasibility of Compounds," *Journal of Combinatorial Chemistry,* American Chemical Society, Nov./Dec. 1999, vol. 1, No. 6, pp. 524–533.

Gasteiger, J. et al, "Assessment of the Diversity of Combinatorial Libraries by an Encoding of Molecular Surface Properties," *Abstracts of Papers Part 1: 217th ACS National Meeting,* Mar. 24–28, 1996, p. 70–CINF.

Hassan, Moises et al., "Optimization and visualization of molecular diversity of combinatorial libraries," *Molecular Diversity,* ESCOM Science Publishers B.V., 1996, vol. 2, pp. 64–74.

Bellman, R.E., *Adaptive Control Processes: A Guided Tour,* Princeton Univ. Press, Princeton, NJ (1961), entire book submitted.

Bezdek, J.C., *Pattern Recognition with Fuzzy Objective Function Algorithms,* Plenum Press, New York, NY (1981), entire book submitted.

Johnson, M.A., and Maggiora, G.M., *Concepts and Applications of Molecular Similarity,* John Wiley and Sons, New York, NY (1990), entire book submitted.

Kohonen, T., *Self–Organizing Maps,* Springer–Verlag, Heidelberg, Germany (1995), entire book submitted.

Oja, E., *Subspace Methods of Pattern Recognition,* Research Studies Press Ltd., Letchworth, England (1983), entire book submitted.

Agrafiotis, D.K., "A New Method For Analyzing Protein Sequence Relationships Based on Sammon Maps," *Protein Science,* Cambridge University Press, vol. 6, No. 2, Feb. 1997, pp. 287–294.

Porto, V. et al., "Alternative Neural Network Training Methods," *IEEE Expert,* IEEE, vol. 10, No. 4, pp. 16–22.

Amzel, L.M., "Structure–Based drug design," *Current Opinion in Biotechnology,* vol. 9, No. 4, Aug. 1998, pp. 366–369.

Blaney, J.M. and Martin, E.J., "Computational approaches for combinatorial library design and molecular diversity analysis," *Current Opinion in Chemical Biology,* Current Biology Ltd., vol. 1, No. 1, Jun. 1997, pp. 54–59.

Mumenthaler, Ch. And Braun, W., "Automated Assignment of Simulated and Experimental NOESY Spectra of Proteins by Feedback Filtering and Self–correcting Distance Geometry," *Journal of Molecular Biology,* Academic Press Limited, vol. 254, No. 3, Dec. 1, 1995, pp. 465–480.

Caflisch, A. and Karplus, M., "Computational combinatorial chemistry for de novo ligand design: Review and assessment," *Perspectives in Drug Discovery and Design,* ESCOM Science Publishers, B.V., vol. 3, 1995, pp. 51–84.

Meng, E. et al., "Orientational Sampling and Rigid–Body Minimization in Molecular Docking," *Proteins: Structure, Function and Genetics,* Wiley–Liss, Inc., vol. 17, No. 3, 1993, pp. 266–278.

Eichier, U. et al., "Addressing the problem of molecular diversity," *Drugs of the Future,* Prous Science, vol. 24, No. 2, 1999, pp. 177–190.

Felder, E.R. and Poppinger, D., "Combinatorial Compound Libraries for Enhanced Drug Discovery Approaches," *Advances in Drug Research,* Academic Press, vol. 30, 1997, pp. 112–199.

Geysen, H.M. and Mason, T.J., "Screening Chemically Synthesized Peptide Libraries for Biologically–Relevant Molecules," *Bioorganic & Medicinal Chemistry Letters,* Pergamon Press Ltd., vol. 3, No. 3, 1993, pp. 397–404.

Gobbi, A. et al., "New Leads By Selective Screening of Compounds From Large Databases," *Abstracts of Papers Part 1: 213th ACS National Meeting,* American Chemical Society, Apr. 13–17, 1997, p. 67–CINF.

Houghten, R.A. et al., "The Use of Synthetic Peptide Combinatorial Libraries for the Identification of Bioactive Peptides," *Peptide Research,* vol. 5, No. 6, 1992, pp. 351–358.

Klopman, G., "Artificial Intelligence Approach to Structure–Activity Studies. Computer Automated Structure Evaluation of Biological Activity of Organic Molecules," *Journal of the American Chemical Society,* American Chemical Society, vol. 106, No. 24, 1984, pp. 7315–7321.

Lajiness, M.S. et al., "Implementing Drug Screening Programs Using Molecular Similarity Methods," *QSAR: Quantitative Structure–Activity Relationships in Drug Design,* Alan R. Liss, Inc., 1989, pp. 173–176.

Loew, G.H. et al., "Strategies for Indirect Computer–Aided Drug Design," *Pharmaceutical Research,* Plenum Publishing Corporation, vol. 10, No. 4, 1993, pp. 475–486.

Lynch, M.F. et al., "Generic Structure Storage and Retrieval," *Journal of Chemical Information and Computer Sciences,* American Chemical Society, vol. 25, No. 3, Aug. 1985, pp. 264–270.

Myers, P.L. et al., "Rapid, Reliable Drug Discovery," *Today's Chemist At Work,* American Chemical Society, vol. 6, No. 7, Jul./Aug. 1997, pp. 46–48, 51 & 53.

Pabo, C.O. and Suchanek, E.G., "Computer–Aided Model–Building Strategies for Protein Design," *Biochemistry,* American Chemical Society, vol. 25, No. 20, 1986, pp. 5987–5991.

Saudek, V. et al., "Solution Conformation of Endothelin–1 by H NMR, CD, and Molecular Modeling," *International Journal of Peptide Protein Research,* Munksgaard International Publishers Ltd., vol. 37, No. 3, 1991, pp. 174–179.

Singh, J. et al., "Application of Genetic Algorithms to Combinatorial Synthesis: A Computational Approach to Lead Identification and Lead Optimization," *J. Am. Chem. Soc.,* American Chemical Society, vol. 118, No. 7, Feb. 7, 1996, pp. 1669–1676.

Van Drie, J.H. and Lajiness, M.S., "Approaches to virtual library design," *Drug Discovery today,* Elsevier Science Ltd., vol. 3, No. 6, Jun. 1998, pp. 274–283.

Walters, W.P. et al., "Virtual screening—an overview," *Drug Discovery today,* Elsevier Science Ltd., vol. 3, No. 4, Apr. 1998, pp. 160–178.

Weber, L., "Evolutionary combinatorial chemistry: application of genetic algorithms," *Drug Discovery today,* Elsevier Science Ltd., vol. 3, No. 8, Aug. 1998, pp. 379–385.

Weber, L. et al., "Optimization of the Biological Activity of Combinatorial Compound Libraries by a Genetic Algorithm," *Angewandte Chemie International Edition in English,* VCH, vol. 34, No. 20, Nov. 3, 1995, pp. 2280–2282.

Graybill, T.L. et al., "Enhancing the Drug Discovery Process by Integration of High–Throughput Chemistry and Structure–Based Drug Design," *Molecular Diversity and Combinatorial Chemistry: Libraries and Drug Discovery.* American Chemical Society, 1996, pp. 16–27.

Saund, E., "Dimensionality–Reduction Using Connectionist Networks," *IEEE Transactions on Pattern Analysis and Machine Intelligence,* IEEE, vol. 11, No. 3, Mar. 1989, pp. 304–314.

"3DP gains drug research patent", *Chemistry in Britain,* The Royal Society of Chemistry, vol. 32, No. 1, Jan. 1996, p. 22.

"Accelerate the Discovery Cycle with Chem–X!", Source and date of publication unclear, 2 pages.

Agrafiotis, D. K., "Stochastic Algorithms for Maximizing Molecular Diversity", *Journal of Chemical Information and Computer Sciences,* American Chemical Society, vol. 37, No. 5, 1997, pp. 841–851.

Alsberg, B.K. et al., "Classification of pyrolysis mass spectra by fuzzy multivariate rule induction–comparison with regression, K–nearest neighbour, neural and decision–tree methods", *Analytica Chimica Acta,* Elsevier Science B.V., vol. 348, No. 1–3, Aug. 20, 1997, pp. 389–407.

Andrea, T.A. and Kalayeh, H., "Applications of Neural Networks in Quantitative Structure–Activity Relationships of Dihydrofolate Reductase Inhibitors", *Journal of Medicinal Chemistry,* American Chemical Society, vol. 34, No. 9, 1991, pp. 2824–2836.

Aoyama, T. et al., "Neural Networks Applied to Quantitative Structure–Activity Relationship Analysis", *Journal of Medicinal Chemistry,* American Chemical Society, vol. 33, No. 9, 1990, pp. 2583–2590.

Aoyama, T. and Ichikawa, H., "Obtaining the Correlation Indices between Drug Activity and Structural Parameters Using a Neural Network", *Chemical & Pharmaceutical Bulletin,* Pharmaceutical Society of Japan, vol. 39, No. 2, Feb. 1991, pp. 372–378.

Leach, A., "A Survey of Methods for Searching the Conformational Space of Small and Medium–Sized Molecules," *Reviews in Computational Chemistry,* VCH Publishers, vol. 2, pp. 1–55.

Baum, R.M., "Combinatorial Approaches Provide Fresh Leads for Medicinal Chemistry", *Chemical & Engineering News,* American Chemical Society, Feb. 7, 1994, pp. 20–26.

Bentley, J. L., "Multidimensional Binary Search Trees Used for Associative Searching", *Communications of the ACM,* Association for Computing Machinery, Inc., vol. 18, No. 9, Sep. 1975, pp. 509–517.

Bottou, L. and Vapnik, V. "Local Learning Algorithms", *Neural Computations,* Massachusetts Insititute of Technology, vol. 4, No. 6, Nov. 1992, pp. 888–900.

Boulu, L.G. and Crippen, G.M., "Voronoi Binding Site Models: Calculation of Binding Modes and Influence of Drug Binding Data Accuracy", *Journal of Computational Chemistry,* John Wiley & Sons, Inc., vol. 10, No. 5, Jul./Aug. 1989, pp. 673–682.

Boulu, L.G. et al., "Voronoi Binding Site Model of a Polycyclic Aromatic Hydrocarbon Binding Protein", *Journal of Medicinal Chemistry,* American Chemical Society, vol. 33, No. 2, 1990, pp. 771–775.

Cacoullos, T., "Estimation of a Multivariate Density", *Annals of The Institute of Statistical Mathematics,* The Institute of Statistical Mathematics, vol. 18, No. 2, 1966, pp. 179–189.

Clark, R.D., "OptiSim: An Extended Dissimilarity Selection Method for Finding Diverse Representative Subsets", *Journal of Chemical Information and Computer Science,* American Chemical Society, vol. 37, No. 6, 1997, pp. 1181–1188.

Clark, D. E., and Westhead, D.R., "Evolutionary algorithms in computer–aided molecular design", *Journal of Computer–Aided Molecular Design,* EXCOM Science Publishers B.V., vol. 10, No. 4, Aug. 1996, pp. 337–358.

Cramer, III, R. D. et al., "Comparative Molecular Field Analyisis (CoMFA). 1. Effect of Shape on Binding of Steroids to Carrier Proteins", *Journal of The American Chemical Society,* Chemical Society, vol. 110, No. 18, Aug. 31, 1988, pp. 5959–5967.

Cramer, III, R. D. et al., "Substructural Analysis. A Novel Approach to the Problem of Drug Design", *Journal of Medicinal Chemistry,* vol. 17, No. 5, May 1974, pp. 533–535.

Crippen, G. M., "Voronoi Binding Site Models", *Journal of Computational Chemistry,* John Wiley & Sons, Inc., vol. 8, No. 7, Oct./Nov. 1987, pp. 943–955.

Friedman, J. H. et al., "An Algorithm for Finding Best Matches in Logarithmic Expected Time", *ACM Transactions on Mathematical Software,* Association for Computing Machinery, vol. 3, No. 3, Sep. 1977, pp. 209–226.

Friedman, J.H., "Fitting Functions To Noisy Data In High Dimensions", Department of Statistics–Stanford University Technical Report No. 101, (Aug., 1988), pp. 1–36.

Gallop, M. A. et al., "Applications of Combinatorial Technologies to Drug Discovery. 1. Background and Peptide Combinatorial Libraries", *Journal of Medicinal Chemistry,* American Chemical Society, vol. 37, No. 9, Apr. 29, 1994, pp. 1233–1251.

Ghose, A. K. and Crippen, G.M., "Use of Physicochemical Parameters in Distance Geometry and Related Three–Dimensional Quantitative Structure–Activity Relationships: A Demonstration Using *Escherichia coli* Dihydrofolate Reductase Inhibitors", *Journal of Medicinal Chemistry,* American Chemical Society, vol. 28, No. 3, 1985, pp. 333–346.

Good, A. C. et al., "Structure–Activity Relationships from Molecular Similarity Matrices", *Journal of Medicinal Chemistry,* American Chemical Society, vol. 36, No. 4, Feb. 19, 1993, pp. 433–438.

Gordon, E. M. et al., "Applications of Combinatorial Technologies to Drug Discovery. 2. Combinatorial Organic Synthesis, Library Screening Strategies, and Future Directions", *Journal of Medicinal Chemistry,* American Chemical Society, vol. 37, No. 10, May 13, 1994, pp. 1385–1401.

Hartigan, J. A., "Representation of Similarity Matrices By Trees", *Journal of the American Statistical Association,* vol. 62, No. 320, Dec. 1967, pp. 1140–1158.

Hopfinger, A. J., "A QSAR Investigation of Dihydrofolate Reductase Inhibition by Baker Triazines Based upon Molecular Shape Analysis", *Journal of the American Chemical Society,* American Chemical Society, vol. 102, No. 24, Nov. 19, 1980, pp. 7196–7206.

Jackson, R. C., "Update on computer–aided drug design", *Current Opinion in Biotechnology,* Current Biology Ltd., vol. 6, No. 6, Dec. 1995, pp. 646–651.

Kim, K. H., "Comparative molecular field analysis (CoMFA)", *Molecular Similarity in Drug Design,* ed. P. M. Dean, Blackie Academic & Professional, 1995, Ch. 12, pp. 291–331.

Kohonen, T., "Self–Organized Formation of Topologically Correct Feature Maps", *Biological Cybernetics,* Springer–Verlag, vol. 43, No. 1, 1982, pp. 59–69.

Koile, K. and Shapiro, R., "Building A Collaborative Drug Design System", *Proceedings of the 25th Hawaii International Conference on System Sciences,* IEEE, 1992, pp. 706–716.

Kowalski, B. R. and Bender, C. F., "Pattern Recognition. II. Linear and Nonlinear Methods for Displaying Chemical Data", *Journal of the American Chemical Society,* American Chemical Society, vol. 95, No. 3, Feb. 7, 1973, pp. 686–693.

Kruskal, J. B., "Nonmetric Multidimensional Scaling: A Numerical Method", *Psychometrika,* vol. 29, No. 2, Jun., 1964, pp. 115–129.

Lengauer, T. and Rarey, M., "Computational methods for biomolecular docking", *Current Opinion in Structural Biology,* Current Biology Ltd, vol. 6, No. 3, Jun., 1996, pp. 402–406.

Luke, B. T., "Evolutionary Programming Applied to the Development of Quantitative Structure–Activity Relationships and Quantitative Structure–Property Relationships", *Journal of Chemical Information and Computer Sciences,* American Chemical Society, vol. 34, No. 6, Nov./Dec. 1994, pp. 1279–1287.

Martin, E. J. et al., "Does Combinatorial Chemistry Obviate Computer–Aided Drug Design?", *Reviews in Computational Chemistry,* VCH Publishers, Inc., vol. 10, 1997, pp. 75–99.

Martin, E. J. et al., "Measuring Diversity: Experimental Design of Combinatorial Libraries for Drug Discovery", *Journal of Medicinal Chemistry,* American Chemical Society, vol. 38, No. 9, Apr. 28, 1995, pp. 1431–1436.

McMartin, C. and Bohacek, R.S., "QXP: Powerful, rapid computer algorithms for structure–based drug design", *Journal of Compter–Aided Molecular Design,* Kluwer Academic Publishers, vol. 11, No. 4, Jul. 1997, pp. 333–344.

Mezey, P. G. and Walker, P.D., "Fuzzy molecular fragments in drug research", *Drug Discovery today,* vol. 2, No. 4, Apr. 1997, pp. 132–137.

Müller, K., "On the paradigm shift from rational to random design", *Journal of Molecular Structure (Theochem)*, Elsevier Science B.V., vol. 398–399, Special Issue, 1997, pp. 467–471.

Jorgensen, W. and Tirado–Rives, J., "Monte Carlo vs. Molecular Dynamics for Conformational Sampling," *Journal of Physical Chemistry*, American Chemical Society, vol. 100, No. 34, Aug. 22, 1996, pp. 14508–14513.

Kuszewski, J. et al., "Sampling and efficiency of metric matrix, distance geometry: A novel partial metrization algorithm," *Journal of Biomolecular NMR*, Escom Science Publishers B.V., vol. 2, No. 1, Jan. 1992, pp. 35–56.

Omohundro, S. M., "Bumptrees for Efficient Function, Constraint, and Classification Learning", *Advances in Neural Information Processing Systems 3*, Morgan Kaufmann, 1991, 7 pages, unknown.

Parrill, A. L., "Evolutionary and genetic methods in drug design", *Drug Discovery today*, Elsevier Science Ltd., vol. 1, No. 12, Dec. 1996, pp. 514–521.

Polanski, J., "A neural network for the simulation of biological systems,", *Journal of Molecular Structure (Theochem)*, Elsevier Science Ltd., vol. 398–399, Special Issue, 1997, pp. 565–571.

Ramos–Nino, M. E. et al., "A comparison of quantitative structure–activity relationships for the effect of benzoic and cinnamic acids on *Listeria monocytogenes* using multiple linear regression, artificial neural network and fuzzy systems", *Journal of Applied Microbiology*, Society for Applied Bacteriology, vol. 82, No. 2, Feb. 1997, pp. 168–176.

Rogers, D. and Hopfinger, A. J., "Application of Genetic Function Approximation to Quantitative Structure–Activity Relationships and Quantitative Structure–Property Relationships", *Journal of Chemical Information and Computer Sciences*, American Chemical Society, vol. 34, No. 4, Jul./Aug. 1994, pp. 854–866.

Sammon, Jr., J. W., "A Nonlinear Mapping for Data Structure Analysis", *IEEE Transactions on Computers*, IEEE, vol. C–18, No. 5, May 1969, pp. 401–409.

Simon, Z. et al., "Mapping of Dihydrofolate–reductase Receptor Site by Correlation with Minimal Topological (Steric) Differences", *Journal of Theoretical Biology*, Academic Press, Inc., vol. 66, No. 3, Jun. 7, 1997, pp. 485–495.

Smellie, A. S. et al., "Fast Drug–Receptor Mapping by Site–Directed Distances: A Novel Method of Predicting New Pharmacological Leads", *Journal of Chemical Information and Computer Sciences*, American Chemical Society, vol. 31, No. 3, Aug. 1991, pp. 386–392.

Specht, D. F., "A General Regression Neural Network", *IEEE Transactions on Neural Networks*, IEEE, vol. 2, No. 6, Nov. 1991, pp. 568–576.

Svozil, D. et al., "Neural Network Prediction of the Solvatochromic Polarity/Polarizability Parameter $\pi^{H}_{2}$", *Journal of Chemical Information and Computer Sciences*, American Chemical Society, vol. 37, No. 2, 1997, pp. 338–342.

Todorov, N. P. and Dean, P. M., "Evaluation of a method for controlling molecular scaffold diversity in de novo ligand design", *Journal of Computer–Aided Molecular Design*, ESCOM Science Publishers B.V., vol. 11, 1997, pp. 175–192.

Torgerson, W. S., "Multidimensional Scaling: I. Theory and Method", *Psychometrika*, The Psychometric Society, vol. 17, No. 4, Dec. 1952, pp. 401–419.

Vapnik, V., "Principles of Risk Minimization for Learning Theory", *Advances in Neural Information Processing Systems, 4*, Morgan Kaufmann Publishers, Inc., 1992, pp. 831–838.

Vapnik, V. and Bottou, L., "Local Algorithms for Pattern Recognition and Dependencies Estimation", *Neural Computation*, Massachuessetts Institute of Technology, vol. 5, No. 6, Nov. 1993, pp. 893–909.

Viswanadhan, V. N. et al., "Mapping the binding site of the nucleoside transporter protein: a 3D–QSAR study", *Biochimica et Biophysica Acta*, Elsevier Science Publishers B.V., vol. 1039, No. 3, 1990, pp. 356–366.

Jain, A. et al., "Artificial Neural Networks: A Tutorial," IEEE, Mar. 1996, pp. 31–44.

Westhead, D. R. et al., "A comparison of heuristic search algorithms for molecular docking", *Journal of Computer–Aided Molecular Design*, Kluwer Academic Publishers, vol. 11, 1997, pp. 209–228.

Willett, P., "Genetic algorithms in molecular recognition and design", *Trends in Biotechnology*, Elsevier Science Publishers B.V., vol. 13, No. 12, Dec. 1995, pp. 516–521.

Willett, P. and Winterman, V., "A Comparison of Some Measures for the Determination of Inter–Molecular Structural Similarity Measures of Inter–Molecular Structural Similarity", *Quantitative Structure–Activity Relationships*, VCH, vol. 5, No. 1, Mar. 1986, pp. 18–25.

Zadeh, L. A., "Communication Fuzzy Algorithms", *Information and Control*, Academic Press Inc., vol. 12, No. 2, Feb. 1968, pp. 94–102.

Zadeh, L. A., "Fuzzy Sets", *Information and Control*, Academic Press Inc., vol. 8, No. 3, Jun. 1965, pp. 338–353.

Havel, T., "A New Method for Building Protein Conformations from Sequence Alignments with Homologues of Known Structure," *Journal of Molecular Biology*, Academic Press Limited, vol. 217, No. 1, Jan. 5, 1991, pp. 1–7.

Havel, T. and Wüthrich, K., "A Distance Geometry Program for Determining the Structures of Small Proteins and other Macromolecules from Nuclear Magnetic Resonance Measurements of Intramolecular $^1$H– $^1$H Proximities in Solution," *Bulletin of Mathematical Biology*, Pergamon Press, vol. 46, No. 4, 1984, pp. 673–698.

Aoyama, T. et al., "Neural Networks Applied to Structure–Activity Relationsihips," *Journal of Medicinal Chemistry*, American Chemical Society, vol. 33., No. 3, 1990, pp. 905–908.

Gasteiger, J. et al., "Analysis of the Reactivity of Single Bonds in Aliphatic Molecules by Statistical and Pattern Recognition Methods," *Journal of Chemical Information and Computer Sciences*, American Chemical Society, vol. 33, No. 3, 1993, pp. 385–394.

Guez, A. and Nevo, I., "Neural networks and fuzzy logic in clinical laboratory computing with application to integrated monitoring," *Clinica Chimica Acta*, Elsevier Science Publishers B.V., vol. 248, 1996, pp. 73–90.

Rouvray, D.H., "Similarity in Chemistry: Past, Present and Future," *Topics in Chemistry*, Springer–Verlag, vol. 173, 1995, pp. 1–30.

de Ridder, D. and Duin, R.P.W., "Sammon's mapping using neural networks: A comparison," *Pattern Recognition Letters,* Elsevier Science Publishers B.V., vol. 18, No. 11–13, 1997, pp. 1307–1316.

Havel, T. and Wüthrich, K., "An Evaluation of the Combined Use of Nuclear Magnetic Resonance and Distance Geometry for the Determination of Protein Conformations in Solution," *Journal of Molecular Biology,* Academic Press Inc., vol. 182, No. 2, Mar. 20, 1985, pp. 281–294.

Chang, G. et al., An Internal Coordinate Monte Carlo Method for Searching Conformational Space, *Journal of the American Chemical Society,* American Chemical Society, vol. III, Jun. 1989, No. 12, pp. 4379–4386.

Crippen, G.M. and Havel, T.F., *Distance Geometry and Molecular Conformation,* Research Studies Press Ltd., 1988, entire book submitted.

Feuston, B. et al., "Comparison of Knowledge–Based and Distance Geometry Approaches for Generation of Molecular Conformations," *Journal of Information and Computer Sciences,* American Chemical Society, vol. 41, No. 3, 2001, pp. 754–763.

Ferguson, D. and Raber, D., "A New Approach to Probing Conformational Space with Molecular Mechanics: Random Incremental Pulse Search," *Journal of the American Chemical Society,* American Chemical Society, vol. 111, No. 12, 1989, pp. 4371–4378.

Halgren, T. and Nachbar, R., "Merck Molecular Force Field. IV. Conformational Energies and Geometries for MMFF94*," *Journal of Computational Chemistry,* John Wiley & Sons, Inc., vol. 17, Nos. 5 & 6, 1996, pp. 587–915.

Halgren, T., "Merck Molecular Force Field. V. Extension of MMFF94 Using Experimental Data, Additional Computational Data, and Empirical Rules*," *Journal of Computational Chemistry,* John Wiley & Sons, Inc., vol. 17, Nos. 5 & 6, Apr. 1996, pp. 616–641.

Huang, E. et al., "Distance geometry generates native–like folds for small helical proteins using the consensus distances of predicted protein structures," *Protein Science,* The Protein Society, vol. 7, No. 9, Sep. 1998, pp. 1998–2003.

| INDEX | DESCRIPTOR | SISO TRAINING $R^2$ | SISO TEST $R^2$ | MISO TRAINING $R^2$ | MISO TEST $R^2$ |
|---|---|---|---|---|---|
| 1 | NO. ATOMS | 0.996 | 0.997 | | |
| 2 | NO. BONDS | 0.995 | 0.996 | | |
| 3 | NO. ELEMENTS | 0.603 | 0.614 | 0.822 | 0.823 |
| 4 | MOLECULAR WEIGHT | 0.996 | 0.997 | | |
| 5 | CHI 0 | 0.996 | 0.997 | | |
| 6 | CHI PATH 1 | 0.996 | 0.997 | | |
| 7 | CHI PATH 2 | 0.994 | 0.995 | | |
| 8 | CHI PATH 3 | 0.971 | 0.973 | | |
| 9 | CHI PATH 4 | 0.974 | 0.976 | | |
| 10 | CHI PATH 5 | 0.956 | 0.957 | | |
| 11 | CHI PATH 6 | 0.909 | 0.910 | | |
| 12 | CHI PATH 7 | 0.837 | 0.843 | 0.943 | 0.942 |
| 13 | CHI PATH 8 | 0.666 | 0.673 | 0.938 | 0.934 |
| 14 | CHI PATH 9 | 0.563 | 0.554 | 0.939 | 0.936 |
| 15 | CHI PATH 10 | 0.447 | 0.457 | 0.950 | 0.950 |
| 16 | CHI CLUSTER 3 | 0.988 | 0.987 | | |
| 17 | CHI CLUSTER 4 | 0.993 | 0.993 | | |
| 18 | CHI PATH/CLUSTER 4 | 0.978 | 0.980 | | |
| 19 | VAL CHI 0 | 0.996 | 0.997 | | |
| 20 | VAL CHI PATH 1 | 0.997 | 0.998 | | |
| 21 | VAL CHI PATH 2 | 0.996 | 0.996 | | |
| 22 | VAL CHI PATH 3 | 0.993 | 0.994 | | |
| 23 | VAL CHI PATH 4 | 0.981 | 0.982 | | |
| 24 | VAL CHI PATH 5 | 0.952 | 0.951 | | |
| 25 | VAL CHI PATH 6 | 0.907 | 0.905 | | |

FIG. 9A

| INDEX | DESCRIPTOR | SISO TRAINING $R^2$ | SISO TEST $R^2$ | MISO TRAINING $R^2$ | MISO TEST $R^2$ |
|---|---|---|---|---|---|
| 26 | VAL CHI PATH 7 | 0.773 | 0.775 | 0.901 | 0.905 |
| 27 | VAL CHI PATH 8 | 0.619 | 0.621 | 0.890 | 0.889 |
| 28 | VAL CHI PATH 9 | 0.349 | 0.328 | 0.910 | 0.910 |
| 29 | VAL CHI PATH 10 | 0.222 | 0.201 | 0.921 | 0.920 |
| 30 | VAL CHI CLUSTER 3 | 0.994 | 0.994 | | |
| 31 | VAL CHI CLUSTER 4 | 0.993 | 0.993 | | |
| 32 | VAL CHI PATH/CLUSTER 4 | 0.988 | 0.989 | | |
| 33 | CHI CHAIN 3 | 1.000 | 1.000 | | |
| 34 | CHI CHAIN 4 | 1.000 | 1.000 | | |
| 35 | CHI CHAIN 5 | 0.979 | 0.978 | | |
| 36 | CHI CHAIN 6 | 0.995 | 0.995 | | |
| 37 | CHI CHAIN 7 | 0.999 | 0.999 | | |
| 38 | CHI CHAIN 8 | 1.000 | 1.000 | | |
| 39 | CHI CHAIN 9 | 0.999 | 0.999 | | |
| 40 | CHI CHAIN 10 | 0.999 | 0.998 | | |
| 41 | VAL CHI CHAIN 3 | 1.000 | 1.000 | | |
| 42 | VAL CHI CHAIN 4 | 1.000 | 1.000 | | |
| 43 | VAL CHI CHAIN 5 | 0.994 | 0.996 | | |
| 44 | VAL CHI CHAIN 6 | 0.994 | 0.995 | | |
| 45 | VAL CHI CHAIN 7 | 0.998 | 0.998 | | |
| 46 | VAL CHI CHAIN 8 | 1.000 | 1.000 | | |
| 47 | VAL CHI CHAIN 9 | 0.997 | 0.998 | | |
| 48 | VAL CHI CHAIN 10 | 0.986 | 0.980 | | |
| 49 | SUBGRAPH COUNT PATH 2 | 0.996 | 0.997 | | |
| 50 | SUBGRAPH COUNT PATH 3 | 0.990 | 0.990 | | |

FIG. 9B

| INDEX | DESCRIPTOR | SISO TRAINING $R^2$ | SISO TEST $R^2$ | MISO TRAINING $R^2$ | MISO TEST $R^2$ |
|---|---|---|---|---|---|
| 51 | SUBGRAPH COUNT PATH 4 | 0.957 | 0.960 | | |
| 52 | SUBGRAPH COUNT PATH 5 | 0.914 | 0.918 | | |
| 53 | SUBGRAPH COUNT PATH 6 | 0.837 | 0.844 | 0.909 | 0.905 |
| 54 | SUBGRAPH COUNT PATH 7 | 0.752 | 0.770 | 0.892 | 0.887 |
| 55 | SUBGRAPH COUNT PATH 8 | 0.582 | 0.599 | 0.907 | 0.906 |
| 56 | SUBGRAPH COUNT PATH 9 | 0.446 | 0.448 | 0.933 | 0.932 |
| 57 | SUBGRAPH COUNT PATH 10 | 0.366 | 0.383 | 0.947 | 0.945 |
| 58 | SUBGRAPH COUNT CLUSTER 3 | 0.994 | 0.995 | | |
| 59 | SUBGRAPH COUNT CLUSTER 4 | 0.991 | 0.991 | | |
| 60 | SUBGRAPH COUNT PATH/CLUSTER 4 | 0.980 | 0.980 | | |
| 61 | SUBGRAPH COUNT RING 3 | 1.000 | 1.000 | | |
| 62 | SUBGRAPH COUNT RING 4 | 1.000 | 1.000 | | |
| 63 | SUBGRAPH COUNT RING 5 | 0.995 | 0.995 | | |
| 64 | SUBGRAPH COUNT RING 6 | 0.994 | 0.995 | | |
| 65 | SUBGRAPH COUNT RING 7 | 1.000 | 1.000 | | |
| 66 | SUBGRAPH COUNT RING 8 | 1.000 | 1.000 | | |
| 67 | SUBGRAPH COUNT RING 9 | 1.000 | 1.000 | | |
| 68 | SUBGRAPH COUNT RING 10 | 0.999 | 0.999 | | |
| 69 | KAPPA 0 | 0.980 | 0.980 | | |
| 70 | KAPPA 1 | 0.991 | 0.992 | | |
| 71 | KAPPA 2 | 0.907 | 0.908 | | |
| 72 | KAPPA 3 | 0.709 | 0.710 | 0.806 | 0.799 |
| 73 | KAPPA ALPHA 1 | 0.987 | 0.987 | | |
| 74 | KAPPA ALPHA 2 | 0.895 | 0.897 | 0.960 | 0.955 |
| 75 | KAPPA ALPHA 3 | 0.685 | 0.686 | 0.774 | 0.770 |

FIG. 9C

| INDEX | DESCRIPTOR | SISO TRAINING $R^2$ | SISO TEST $R^2$ | MISO TRAINING $R^2$ | MISO TEST $R^2$ |
|---|---|---|---|---|---|
| 76 | WIENER PATH NO. | 0.967 | 0.965 | | |
| 77 | TOTAL WIENER PATH NO. | 0.903 | 0.892 | | |
| 78 | SHANNON INDEX | 0.911 | 0.911 | | |
| 79 | TOTAL NO. OF PATHS | 0.939 | 0.932 | | |
| 80 | BONCHEV-TRINAJSTIĆ IdW INDEX | 0.958 | 0.955 | | |
| 81 | BONCHEV-TRINAJSTIĆ MEAN IdW INDEX | 0.972 | 0.972 | | |
| 82 | BONCHEV-TRINAJSTIĆ IdC INDEX | 0.979 | 0.978 | | |
| 83 | BONCHEV-TRINAJSTIĆ MEAN IdC INDEX | 0.793 | 0.773 | 0.707 | 0.759 |
| 84 | WIENER PARITY NO. | 0.988 | 0.989 | | |
| 85 | PLATT F NO. | 0.996 | 0.997 | | |
| 86 | DELTA PARTITION 1 | 0.996 | 0.996 | | |
| 87 | DELTA PARTITION 2 | 0.992 | 0.992 | | |
| 88 | DELTA PARTITION 3 | 0.997 | 0.997 | | |
| 89 | DELTA PARTITION 4 | 0.995 | 0.996 | | |
| 90 | DELTA PARTITION 5 | 1.000 | 1.000 | | |
| 91 | DELTA PARTITION 6 | 1.000 | 1.000 | | |
| 92 | NO. H | 0.996 | 0.997 | | |
| 93 | NO. B | 1.000 | 1.000 | | |
| 94 | No. C | 0.997 | 0.998 | | |
| 95 | No. N | 0.995 | 0.995 | | |
| 96 | No. O | 0.994 | 0.993 | | |
| 97 | No. F | 0.996 | 0.996 | | |
| 98 | No. Si | 1.000 | 1.000 | | |
| 99 | No. P | 0.999 | 0.999 | | |

FIG. 9D

| INDEX | DESCRIPTOR | SISO TRAINING $R^2$ | SISO TEST $R^2$ | MISO TRAINING $R^2$ | MISO TEST $R^2$ |
|---|---|---|---|---|---|
| 100 | No. S | 0.997 | 0.999 | | |
| 101 | No. Cl | 0.997 | 0.997 | | |
| 102 | No. Ge | 1.000 | 1.000 | | |
| 103 | No. As | 1.000 | 1.000 | | |
| 104 | No. Se | 1.000 | 1.000 | | |
| 105 | No. Br | 1.000 | 1.000 | | |
| 106 | No. I | 1.000 | 1.000 | | |
| 107 | NO. HALOGENS | 0.997 | 0.998 | | |
| 108 | TOTAL TOPOLOGICAL STATE 1 | 0.924 | 0.918 | | |
| 109 | TOTAL TOPOLOGICAL STATE 2 | 0.947 | 0.945 | | |
| 110 | TOTAL TOPOLOGICAL STATE 3 | 0.904 | 0.888 | | |
| 111 | TOTAL TOPOLOGICAL STATE 4 | 0.956 | 0.956 | | |
| 112 | TOTAL TOPOLOGICAL STATE 5 | 0.852 | 0.826 | 0.915 | 0.907 |
| 113 | TOTAL TOPOLOGICAL STATE 6 | 0.980 | 0.980 | | |
| 114 | TOTAL TOPOLOGICAL STATE 7 | 0.832 | 0.790 | 0.914 | 0.889 |
| 115 | TOTAL TOPOLOGICAL STATE 8 | 0.988 | 0.988 | | |
| 116 | TOTAL TOPOLOGICAL STATE 9 | 0.913 | 0.909 | | |
| 117 | TOTAL TOPOLOGICAL STATE 10 | 0.922 | 0.918 | | |

FIG. 9E

| LEAD | RANDOM SIMILARITY | DIRECT SIMILARITY | SISO/MISO SIMILARITY | SISO/MISO IDENTITY | PC-MISO SIMILARITY | PC-MISO INDENTITY |
|---|---|---|---|---|---|---|
| 1 | 1.754 | 0.480 | 0.501 | 69% | 0.486 | 86% |
| 2 | 1.158 | 0.238 | 0.279 | 56% | 0.244 | 83% |
| 3 | 1.664 | 0.655 | 0.680 | 64% | 0.660 | 84% |
| 4 | 1.291 | 0.179 | 0.213 | 60% | 0.186 | 76% |
| 5 | 1.763 | 0.327 | 0.335 | 82% | 0.334 | 83% |
| 6 | 1.196 | 0.201 | 0.224 | 58% | 0.209 | 75% |
| 7 | 1.294 | 0.274 | 0.291 | 72% | 0.283 | 77% |
| 8 | 1.385 | 0.268 | 0.288 | 73% | 0.275 | 84% |
| 9 | 1.694 | 0.464 | 0.481 | 74% | 0.470 | 86% |
| 10 | 1.613 | 0.460 | 0.470 | 79% | 0.464 | 87% |

FIG.10

METHOD, SYSTEM, AND COMPUTER PROGRAM PRODUCT FOR DETERMINING PROPERTIES OF COMBINATORIAL LIBRARY PRODUCTS FROM FEATURES OF LIBRARY BUILDING BLOCKS

CROSS-REFERENCE TO RELATED APPLICATIONS

This application claims the benefit of U.S. Provisional Application No. 60/226,682, filed Aug. 22, 2000, U.S. Provisional Application No. 60/235,937, filed Sep. 28, 2000, and U.S. Provisional Application No. 60/274,238, filed Mar. 9, 2001, each of which is incorporated by reference herein in its entirety.

The following application of common assignee is related to the present application, and is incorporated by reference herein in its entirety:

"System, Method and Computer Program Product For Fast and Efficient Searching of Large Chemical Libraries," Ser. No. 09/506,741, filed Feb. 18, 2000.

FIELD OF THE INVENTION

The present invention relates to combinatorial chemistry and computer aided molecular design. The present invention also relates to pattern analysis, information representation, information cartography and data mining. In particular, the present invention relates to predicting measurable or computed properties of products in a combinatorial chemical library based on features of their corresponding reagents.

BACKGROUND OF THE INVENTION

Algorithmic efficiency has been a long-standing objective in computational drug design. There is perhaps no other problem in chemistry where the need for efficiency is as pressing as in combinatorial chemistry. As will be understood by a person skilled in the relevant art, a significant bottleneck in the virtual screening of a large combinatorial chemical library is the explicit enumeration of products and the calculation of their pertinent properties.

Whether it is based on molecular diversity, molecular similarity, structure-activity correlation, or structure-based design, the design of a combinatorial experiment typically involves the enumeration of every possible product in a virtual library, and the computation of key molecular properties that are thought to be pertinent to the application at hand. (See, e.g., Agrafiotis, D. K., The diversity of chemical libraries, *The Encyclopedia of Computational Chemistry*, Schleyer, P. v. R., Allinger, N. L., Clark, T., Gasteiger, J., Kollman, P. A., Schaefer III, H. F., and Schreiner, P. R., Eds., John Wiley & Sons, Chichester, 742–761 (1998); and Agrafiotis, D. K., Myslik, J. C., and Salemme, F. R., Advances in diversity profiling and combinatorial series design, *Mol. Diversity*, 4(1), 1–22 (1999), each of which is incorporated by reference herein in its entirety).

Several product-based methodologies for screening virtual libraries have been developed. (See, e.g., Sheridan, R. P., and Kearsley, S. K., Using a genetic algorithm to suggest combinatorial libraries, *J. Chem. Info. Comput. Sci.*, 35, 310–320 (1995); Weber, L., Wallbaum, S., Broger, C., and Gubernator, K., Optimization of the biological activity of combinatorial compound libraries by a genetic algorithm, *Angew. Chem. Int. Ed. Eng.*, 34, 2280–2282 (1995); Singh, J., Ator, M. A., Jaeger, E. P., Allen, M. P., Whipple, D. A., Soloweij, J. E., Chowdhary, S., and Treasurywala, A. M., Application of genetic algorithms to combinatorial synthesis: a computational approach for lead identification and lead optimization, *J. Am. Chem. Soc.*, 118, 1669–1676 (1996); Agrafiotis, D. K., Stochastic algorithms for maximizing molecular diversity, *J. Chem. Info. Comput. Sci.*, 37, 841–851 (1997); Brown, R. D., and Martin, Y. C., Designing combinatorial library mixtures using genetic algorithms, *J. Med. Chem.*, 40, 2304–2313 (1997); Murray, C. W., Clark, D. E., Auton, T. R., Firth, M. A., Li, J., Sykes, R. A., Waszkowycz, B., Westhead, D. R. and Young, S. C., PRO__SELECT: combining structure-based drug design and combinatorial chemistry for rapid lead discovery. 1. Technology, *J. Comput.-Aided Mol. Des.*, 11, 193–207 (1997); Agrafiotis, D. K., and Lobanov, V. S., An efficient implementation of distance-based diversity metrics based on k-d trees, *J Chem. Inf. Comput. Sci.*, 39, 51–58 (1999); Gillett, V. J., Willett, P., Bradshaw, J., and Green, D. V. S., Selecting combinatorial libraries to optimize diversity and physical properties, *J Chem. Info. Comput. Sci.*, 39, 169–177 (1999); Stanton, R. V., Mount, J., and Miller, J. L., Combinatorial library design: maximizing model-fitting compounds with matrix synthesis constraints, *J Chem. Info. Comput. Sci.*, 40, 701–705 (2000); and Agrafiotis, D. K., and Lobanov, V. S., Ultrafast algorithm for designing focused combinatorial arrays, *J Chem. Info. Comput. Sci.*, 40, 1030–1038 (2000), each of which is incorporated by reference herein in its entirety).

These product-based methodologies become impractical, however, when they are applied to large combinatorial libraries, i.e. libraries that contain a large number of possible products. In such cases, the most common solution is to restrict attention to a smaller subset of products from the virtual library, or to consider each substitution site independently of all the others. (See, e.g., Martin, E. J., Blaney, J. M., Siani, M. A., Spellmeyer, D. C., Wong, A. K., and Moos, W. H., *J Med. Chem.*, 38, 1431–1436 (1995); Martin, E. J., Spellmeyer, D. C., Critchlow, R. E. Jr., and Blaney, J. M., *Reviews in Computational Chemistry*, Vol. 10, Lipkowitz, K. B., and Boyd, D. B., Eds., VCH, Weinheim (1997); and Martin, E., and Wong, A., Sensitivity analysis and other improvements to tailored combinatorial library design, *J. Chem. Info. Comput. Sci.*, 40, 215–220 (2000), each of which is incorporated by reference herein in its entirety). Unfortunately, the latter approach, which is referred to as reagent-based design, often produces inferior results in terms of meeting the primary design objectives. (See, e.g., Gillet, V. J., Willett, P., and Bradshaw, J., *J. Chem. Inf. Comput. Sci.*; 37(4), 731–740 (1997); and Jamois, E. A., Hassan, M., and Waldman, M., Evaluation of reagent-based and product-based strategies in the design of combinatorial library subsets, *J. Chem. Inf. Comput. Sci.*, 40, 63–70 (2000), each of which is incorporated by reference herein in its entirety).

Hence there is a need for methods, systems, and computer program products that can be used to screen large combinatorial chemical libraries, which do not have the limitations discussed above.

SUMMARY OF THE INVENTION

The present invention provides a method, system, and computer program product for determining properties of combinatorial library products from features of library building blocks.

As described herein, at least one feature is determined for each building block of a combinatorial library having a plurality of products. A training subset of products is selected from the plurality of products of the combinatorial library, and at least one property is determined for each product of the training subset of products. A building block set is identified for each product of the training subset of products, and an input features vector is formed for each product of the training subset of products. A supervised machine learning approach is used to infer a mapping function that transforms the input features vector for each product of the training subset of products to the corresponding at least one property for each product of the training subset of products. After the mapping function is inferred, it is used for determining, estimating, or predicting properties of other products of the library. Properties of other products are determined, estimated, or predicted from their corresponding input features vectors using the inferred mapping function. Building block sets are identified for a plurality of additional products of the combinatorial library. Input features vectors are formed for the plurality of additional products. The input features vectors for the plurality of additional products are transformed using the mapping function to obtain at least one estimate property for each of the plurality of additional products.

In embodiments of the invention, both measured values and/or computed values are used as features for the building blocks of the combinatorial library. Both measured values and/or computed values are also used as properties for the products of the training subset. In embodiments of the invention, at least one of the features of the building blocks is the same as at least one of the properties of the products.

In an embodiment of the invention, the mapping function is implemented using a multilayer perceptron. The multilayer perceptron is trained to implement the mapping function using the input features vector and the corresponding at least one property for each product of the training subset of products.

In an embodiment of the invention, the building blocks of the combinatorial library include reagents used to construct the combinatorial library. In other embodiments, the building blocks of the combinatorial library include fragments of the reagents used to construct the combinatorial library. In still other embodiments, the building blocks of the combinatorial library include modified fragments of the reagents used to construct the combinatorial library.

Further embodiments, features, and advantages of the present invention, as well as the structure and operation of the various embodiments of the present invention, are described in detail below with reference to the accompanying figures.

BRIEF DESCRIPTION OF THE DRAWINGS/FIGURES

The file of this patent contains at least one drawing executed in color. Copies of this patent with color drawing(s) will be provided by the Patent and Trademark Office upon request and payment of the necessary fee.

The present invention is described with reference to the accompanying drawings wherein:

FIGS. 1A–B illustrate a flowchart of a method for determining properties of combinatorial products from a combinatorial library according to an embodiment of the present invention;

FIGS. 9A–9E illustrate a table of example estimation of descriptor properties of combinatorial products by trained single-output networks according to the invention;

FIG. 10 illustrates a table of average similarity scores and percent identity for 10 sets of 1000 compounds most similar to 10 randomly chosen 'leads' as selected by various methodologies from a 6.29 million-member Ugi virtual library according to the invention;

DETAILED DESCRIPTION OF THE INVENTION

Figure 1A:
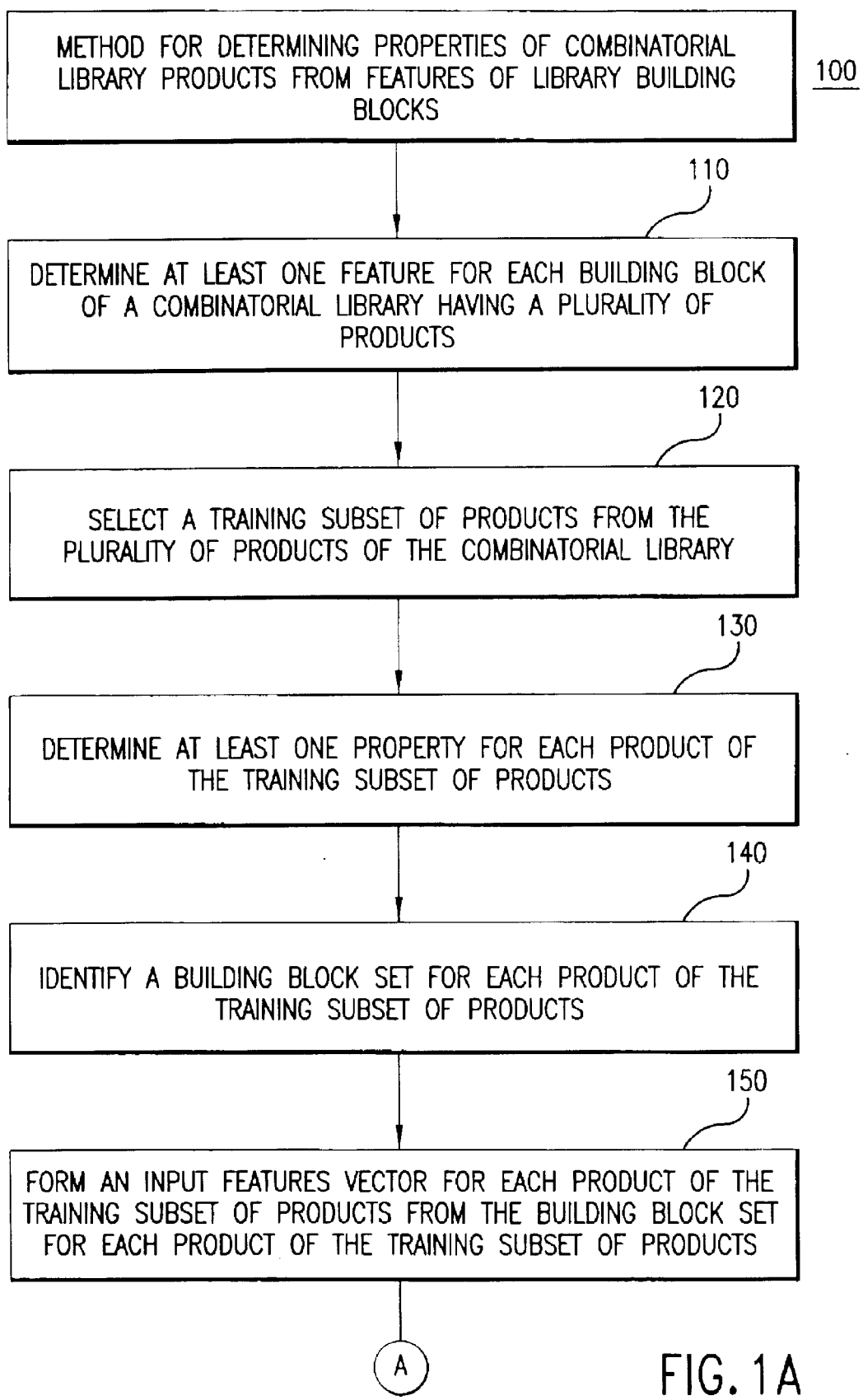

Embodiments of the present invention are now described with references to the figures, where like reference numbers indicate identical or functionally similar elements. Also in the figures, the left most digit(s) of each reference number corresponds to the figure in which the reference number is first used. While specific configurations and arrangements are discussed, it should be understood that this is done for illustrative purposes only. One skilled in the relevant art will recognize that other configurations and arrangements can be used without departing from the spirit and scope of the invention. It will also be apparent to one skilled in the relevant art(s) that this invention can also be employed in a variety of other devices and applications.

Overview of the Invention

The present invention learns to determine, estimate, or predict values associated with properties of combinatorial library products from features of library building blocks. In operation, at least one feature of the building blocks is determined, retrieved, or obtained. A training subset of products is selected from the products, and values for at least one property is determined, retrieved, or obtained for each product of the training subset. A building block set is identified for each product of the training subset, and an input features vector is formed for each product of the training subset. A supervised machine learning approach is used to infer a mapping function that transforms the input features vector for each product of the training subset to the corresponding value of at least one property for each product of the training subset. After the mapping function is inferred, it is used for determining, estimating, or predicting properties of other products of the library from their corresponding input features vectors.

Method Embodiment of the Invention

In an embodiment, the present invention is applied to an electronic library of chemical compounds. The invention is not, however, limited to this example.

A combinatorial chemical library is a collection of chemical compounds or "products" generated by combining a number of chemical "building blocks" such as reagents. For example, a linear combinatorial chemical library such as a polypeptide library is formed by combining a set of chemical building blocks called amino acids in every possible or nearly every possible way for a given compound length (i.e., the number of amino acids in a polypeptide compound). Millions of products theoretically can be synthesized through such combinatorial mixing of building blocks. One commentator has observed that the systematic, combinatorial mixing of 100 interchangeable chemical building blocks results in the theoretical synthesis of 100 million tetrameric compounds or 10 billion pentameric compounds (Gallop et al., "Applications of Combinatorial Technologies to Drug Discovery, Background and Peptide Combinatorial Libraries," J. Med. Chem. 37, 1233–1250 (1994), which is incorporated by reference herein in its entirety). As will be understood by a person skilled in the relevant art, a combinatorial library can be mathematically represented as combinatorial library P, $\{pi_{ij} \ldots i_{ij} \ldots i_{rj}, i=1,2,\ldots,r; j=1,2,\ldots,r_i\}$, wherein r represents the number of variation sites in the combinatorial library P, and $r_i$ represents the number of building blocks at the i-th variation site.

As used herein, the term "building blocks" refers to reagents, fragments of reagents, and/or modified fragments of reagents. In an embodiment of the invention, the building blocks of the combinatorial library comprise the reagents used to construct the combinatorial library. In other embodiments, the building blocks may comprise fragments of the reagents used to construct the combinatorial library and/or modified fragments of the reagents used to construct the combinatorial library.

Figure 1B:
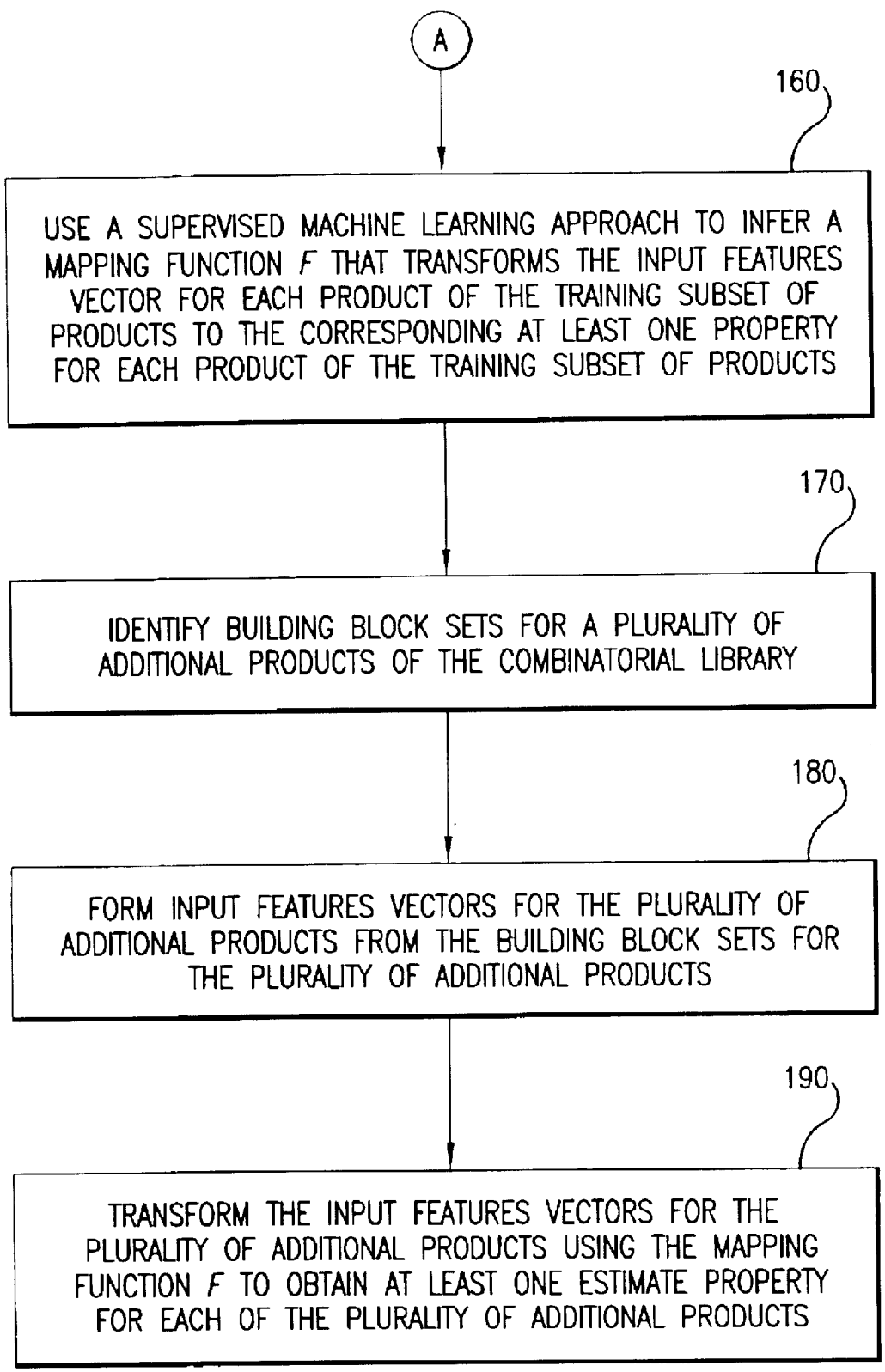
Figure 2:
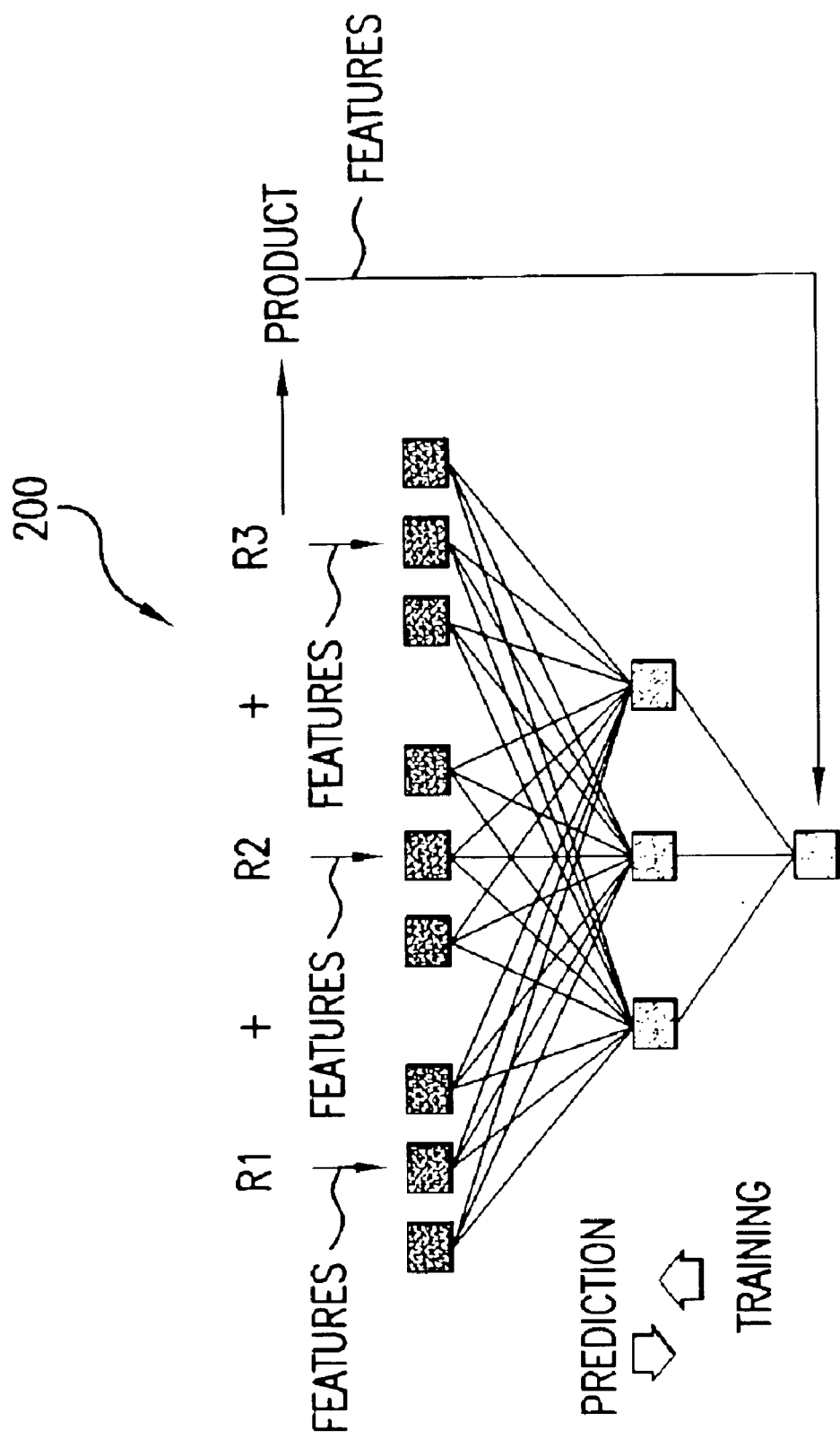
FIG. 2 illustrates an example combinatorial neural network according to an embodiment of the present invention.

FIGS. 1A and 1B illustrate a flowchart of the steps of a method 100 for determining, estimating, or predicting measurable or computable properties of products in a combinatorial chemical library based on features of their corresponding reagents. Method 100 will now be described with reference to the steps illustrated in FIGS. 1A and 1B.

In step 110, at least one feature (descriptor) is determined for each building block of a combinatorial library having a plurality of products $\{a_{ijk}, i=1,2,\ldots,r; j=1,2,\ldots,r_i; k=1,2,\ldots,n_i\}$, wherein r represents the number of variation sites in the combinatorial library P, $r_i$ represents the number of building blocks at the i-th variation site, and $n_i$ represents the number of features used to characterize each building block at the i-th variation site. As used herein, a feature value can be determined, for example, by computing a value or by retrieving a previously calculated or measured value from a storage medium.

In an embodiment of the invention, topological descriptors are computed as building block features. In another embodiment of the invention, the principal components required to capture 99% of the total variance are computed from the topological descriptors calculated for the building blocks. Other example descriptors or features that can be determined include quantum mechanical properties, pharmacophoric properties, BCUT properties and/or other molecular properties. Still other descriptors or features that can be determined will be known to persons skilled in the relevant arts given the description of the invention herein.

In an embodiment of the invention, at least one of the features of the building blocks is a calculated value. In another embodiment, at least one of the features of the building blocks is a measured value. In either embodiment, the feature values can be obtained or retrieved, for example, from an information storage device.

In step 120, a training subset of products is selected from the plurality of products of the combinatorial library. In an embodiment, a training subset of products $\{p_i, i=1,2,\ldots, m; p_i \in P\}$ may be selected from a combinatorial library P. This training subset of products can be chosen in several manners. For example, the training subset of products can be chosen randomly. In another embodiment, the training subset of products can be chosen using a combinatorial design method. In yet another embodiment, the training subset of products can be chosen using a diversity based selection technique. In a case of random selection, the composition of a particular training subset has little influence on the quality of an inferred mapping as long as the training subset is sufficiently large. As will be understood by a person skilled in the relevant arts given the description herein, the size of a training subset depends on the size of the combinatorial library and on the number of variation sites in the library in question.

In step 130, at least one property (descriptor) is determined for each product of the training subset of products. As used herein, a property value can be determined, for example, by computing or by retrieving a previously calculated or measured value from a storage medium. In an embodiment, q properties are determined for each compound $p_i$ in the selected training subset of products, $y_i = \{y_{ij}, i=1,2,\ldots,m, j=1,2,\ldots,q\}$, wherein q is greater or equal to one.

In an embodiment of the invention, at least one of the properties of the products is a calculated value. In another embodiment, at least one of the properties of the products is a measured value. In either embodiment, the property values can be obtained or retrieved, for example, from an information storage device. In an embodiment, at least one of the features of the building blocks determined in step 110 is the same as at least one of the properties of the products determined in step 130. In another embodiment, none of the features of the building blocks determined in step 110 is the same as any of the properties of the products determined in step 130.

In step 140, a building block set is identified for each product of the training subset of products. As used herein, the term "building block set" refers to the at least one reagent, fragment of a reagent, and/or modified fragment of a reagent used to generate a product. The build block set for a particular product is referred to herein as corresponding to the product.

In an embodiment, the corresponding building blocks $\{t_{ij}, t_{ij}=1,2,\ldots,r_j, j=1,2,\ldots,r\}$ are identified for each product $p_i$ of the training subset of products selected from the combinatorial library P.

In step 150, an input features vector is formed for each product of the training subset of products. As used herein, the term "input features vector" refers to a single vector for a particular product of the combinatorial library formed by concatenating the features determined in step 110 for each of the one or more building blocks that make up the product's building block set. In an embodiment, building block features (e.g., reagent descriptors) are concatenated into a single array and presented to a combinatorial neural network according to the invention in the same order.

In an embodiment, for the combinatorial library P described above, input features vectors are formed by concatenating the features, determined in step 110, for the building blocks $\{t_{ij}, t_{ij}=1, 2, \ldots, r_j, j=1, 2, \ldots, r\}$ that are identified for each product $p_i$ into a single vector $\{x_i = a_{1t_{i1}}|a_{2t_{i2}}| \ldots |a_{rt_{ir}}\}$.

In step 160, a supervised machine learning approach is used to infer a mapping function that transforms the input features vector for each product of the training subset of products to the corresponding at least one property for each product of the training subset of products. In an embodiment, step 160 comprises the step of training a combinatorial neural network or a multilayer perceptron according to the invention, using the input features vector and the corresponding at least one property for each product of the training subset of products, to implement the mapping function. This may be represented mathematically as using a supervised machine learning approach to infer a mapping function $f$ that transforms input values $x_i$ to output values $y_i$ from input/output pairs in a training set $T=\{(x_i, y_i), i=1,2, \ldots, m\}$.

As described herein, embodiments of the invention uses a special class of neural networks, referred to herein as combinatorial networks or combinatorial neural networks (CNNs), that are trained to determine, estimate, or predict the properties of combinatorial products from the features of their respective building blocks. Generally speaking, a combinatorial network comprises an input layer containing $n_1 \times n_2 \times \ldots \times n_r$ neurons, where r is the number of variation sites in the combinatorial library and $n_i$ is the number of features used to characterize each building block at the i-th variation site. A typical combinatorial network may comprise one or more hidden layers that contain at least 2 neurons, depending on the complexity of the transformation, and an output layer having a single neuron for each product feature predicted by the network.

In an embodiment of the invention, three-layer, fully connected multilayer perceptrons (MLPs) are used to form a combinatorial network. These networks can be trained using a standard error back-propagation algorithm (see, e.g., S. Haykin, Neural Networks, Macmillan, New York (1994), which is incorporated by reference herein in its entirety), and a logistic transfer function $f(x)=1/(1+e^{-x})$ can be used for both hidden and output layers. In accordance with the invention, each combinatorial network can be trained for a fixed number of epochs or until a predefined error threshold is met using, for example, a linearly decreasing learning rate from 1.0 to 0.01 and a fixed momentum of 0.8. During each epoch, the training patterns or samples can be presented to the network in a randomized order. In other embodiments, other combinatorial networks are used.

After a combinatorial network according to the invention is trained, analyzing or screening the combinatorial library (or any subset thereof) involves computing or retrieving precomputed features of building blocks, concatenating them into an input feature vector and feeding the input feature vector through the trained combinatorial network, which outputs estimate or predicted properties for the products. The estimate or predicted properties can then be used for any subsequent analysis, searching, or classification. As will be understood by a person skilled in the relevant art given the description herein, the present invention can be applied to a wide variety of molecular properties, regardless of origin and complexity.

Step 160 ends when the mapping function is inferred or a CNN is trained to implement the mapping function.

In step 170, building block sets are identified for a plurality of additional products of the combinatorial library. This step is similar to step 140 above.

In step 180, input features vectors are formed for the plurality of additional products. This step is similar to step 150 above.

In an embodiment, steps 170 and 180 involve identifying, after the mapping function $f$ is determined, for a product $p_z \in P$, the corresponding reagents $\{t_{zj}, j=1, 2, \ldots, r\}$ and concatenating their features, $a_{1t_{z1}}, a_{2t_{z2}}, \ldots, a_{rt_{zr}}$, into a single vector $\{x_z = a_{1t_{z1}}|a_{2t_{z2}}| \ldots |a_{rt_{zr}}\}$.

In step 190, the input features vectors for the plurality of additional products are transformed using the mapping function of step 160 to obtain at least one estimate property for each of the plurality of additional products. This can be represented mathematically as mapping $x_z \rightarrow y_z$, using the mapping function (e.g., mapping function $f$) determined in step 160, wherein $y_z$ represents the properties of product $p_z$. In embodiments of the invention, the estimate or predicted properties are stored for subsequent retrieval and analysis.

As will be understood by a person skilled in the relevant art given the description herein, in embodiments, the invention can be used to estimate or predict quantum mechanical properties of combinatorial compounds from quantum mechanical and/or other molecular properties of their respective building blocks. For example, the following quantum mechanical properties can be predicted according to the invention: molecular orbital energies; total electronic energy; total energy; heat of formation; ionization potential; and dipole moment.

In other embodiments, the invention can be used to predict BCUT properties (eigenvalues) of combinatorial compounds from BCUT and/or other molecular properties of their respective building blocks. As would be known to a person skilled in the relevant art, a BCUT value is an eigenvalue. As explained by R. S. Pearlman of the University of Texas, College of Pharmacy, the strength of intermolecular interactions depends on atomic charges, atomic polarizabilities, and atomic H-bond-abilities. Thus, Pearlman proposes constructing three classes of matrices to represent compounds: one class with atomic charge-related values on the diagonal, a second class with atomic polarizability-related values on the diagonal, and a third class with H-bond-abilities on the diagonal. Pearlman also proposed using a variety of additional definitions for the off-diagonal elements including functions of interatomic distance, overlaps, computed bond-orders, etc. (See, e.g., R. S. Pearlman, *Novel Software Tools for Addressing Chemical Diversity*, World Wide Web Address: netsci.org/Science/Combichem/feature08.html.) According to pearlman, the lowest and highest eigenvalues (i.e., BCUT values) of these matrices reflect aspects of molecular structure.

In embodiments, the invention can also be used to predict pharmacophoric properties of combinatorial compounds from pharmacophoric and/or other molecular properties of their respective building blocks. As would be known to a person skilled in the relevant art, a pharmacophore is the spatial mutual orientation of atoms or groups of atoms assumed to be recognized by and interact with a receptor or the active site of a receptor. A receptor can be envisioned as a macromolecular structure such as a protein, an enzyme or a polynucleotide being an integral part of the complex molecular structure of the cellular membrane in which it is anchored or associated with. The recognition elements or receptor sites are oriented in such a way that recognition of and interaction with ligands can take place, leading to a pharmacological effect.

As will be understood by a person skilled in the relevant art given the description herein, the invention is not limited to being used to predict just the above properties of combinatorial compounds from the properties of their respective building blocks. For example, the invention can be used to estimate or predict the 117 topological descriptors listed in FIGS. 9A–E. The invention can also be used to predict many other properties of combinatorial compounds from the properties of their respective building blocks.

Results and Discussion

In this section, the results obtained for embodiments of the method of the invention are presented and discussed. Three different combinatorial network architectures according to the invention were examined using the two combinatorial libraries described below. The network architectures examined were: (1) networks that take as input a single feature (descriptor) from each reagent and produce a single property (descriptor) for the product, (2) networks that take as input multiple features (descriptors) from each reagent and produce a single property (descriptor) for the product, and (3) networks that take as input multiple features (principal components) from each reagent and produce a single property (principle component) for the product. The first architecture category is referred to herein as single-input single-output (SISO) perceptrons. The second and third architecture categories are referred to herein as multiple-input single-output (MISO) perceptrons.

The performance of each architecture was evaluated using three statistical measures: (1) the correlation coefficient between the actual and predicted properties of the products (descriptors), (2) the amount of distortion of the similarity matrix as measured by Pearson correlation coefficient, and (3) the effect of that distortion on similarity searching and context-based retrieval. As a person skilled in the relevant art would know, similarity searching represents the most common form of virtual screening. It is based on the 'similar property principle', i.e. the fundamental belief that structurally similar compounds tend to exhibit similar physico-chemical and biological properties. (See Johnson, M. A., and Maggiora, G. M., *Concepts and Applications of Molecular Similarity*, Wiley (1990), which is incorporated by reference herein in its entirety). Thus, given a set of compounds with some desired biological effect, one seeks to identify similar compounds, expecting that some of them will be more potent, more selective, or more suitable in some other way than the original leads. For purposes of the evaluation described herein, the similarity between two compounds or products was measured by their Euclidean distance in the multidimensional space (see Willett, P.; Barnard, J. M.; Downs, G. M. Chemical Similarity Searching, *J. Chem. Info. Comput. Sci.*, 38, 983–996 (1998), which is incorporated by reference herein in its entirety) formed by the principal components that preserved 99% of the variance in the original topological features.

The simplest of the architectures involves a series of networks, each of which is trained to predict the value of a single product descriptor from the values of that descriptor of the corresponding reagents. Thus, for a library with r components, each product descriptor is estimated by a SISO network with r input and 1 output nodes, hereafter denoted r-h-1, where h is the number of hidden nodes. This approach offers simplicity and ease of training, as well as access to the individual product descriptors. As illustrated in FIGS. 9A–9E, this embodiment of the invention works well for about 80% of the 117 topological descriptors used to evaluate the invention. About 20% of the descriptors listed in FIGS. 9A–9E were not predicted reliably using this embodiment.

The ability of CNNs according to the invention to estimate individual descriptors can be improved by increasing the number of synaptic parameters and by adding to the training data other reagent descriptors that can provide additional information needed for successful prediction. This leads to a network topology of the form rxn-h-1, where n is the number of input descriptors per reagent. The additional descriptors used with this embodiment of the invention can be chosen in a variety of ways. For example, one can employ a feature selection algorithm similar to that used in stepwise regression analysis. This involves trying all possible pairs of descriptors and select the best pair, then trying all possible triplets keeping the first two descriptors fixed and select the best triplet, and continuing in this manner until a predefined number of descriptors of error threshold is met. In practice, however, this rather intensive algorithm is unnecessary. Good results can be obtained using the following approach. First, the correlation coefficients between each reagent and each product descriptor are calculated, and a series of SISO networks are trained in the manner described herein. Then, for each product descriptor that cannot be adequately modeled (e.g., one having a training $R^2$ less than 0.9), the two reagent descriptors that are most highly correlated to that product descriptor are added to the training data, and a new MISO network is trained. When applied to the Ugi library (see FIG. 11), this approach resulted in an array of neural networks that were able to predict all 117 descriptors with high accuracy for both the training and test sets (see FIGS. 9A–9E). As illustrated in FIGS. 9A–9E, the correlation coefficients between the actual and predicted descriptors ranged from about 0.77 to 1.0. The smaller values are typically associated with more complex properties such as the Bonchev-Trinajstic information index $\bar{I}_D{}^c$ (see Bonchev, D. and Trinajstić, N., *J. Chem. Phys.* 67, 4517–4533 (1977), which is incorporated by reference herein in its entirety) and the Kappa shape index $^3\kappa\alpha$ (see Hall L. H. and Kier, L. B, The Molecular Connectivity Chi Indexes and Kappa Shape Indexes in Structure-Property Relations, in *Reviews of Computational Chemistry*, Boyd, D. B. and Lipkowitz, K. B., Eds., VCH Publishers, Chapter 9, 367–422 (1991), which is incorporated by reference herein in its entirety).

To assess the impact on molecular similarity, the optimized networks were used in a feed-forward manner to estimate the descriptors of all 6.29 million compounds in the Ugi library. These descriptors were subsequently decorrelated using the rotation matrix derived from the training set, and the Pearson correlation coefficient of the resulting pairwise distances was computed. This statistic, which measures the correlation between the similarity coefficients computed with the two sets of descriptors (calculated vs. estimated), had a value of 0.99, indicating a nearly perfect reproduction. As used herein, the term 'calculated' refers to descriptors computed with the conventional method, and the term 'estimated' refers to the descriptors generated by the neural networks.

This accuracy was also reflected in the context of similarity searching, using 10 randomly chosen compounds from the Ugi library as 'leads.' In particular, the 1000 most similar compounds to each of these leads were identified using the PCs derived from both the calculated and estimated descriptors, and their similarity scores were compared. FIG. 10 shows a summary of the results obtained.

Figure 3:
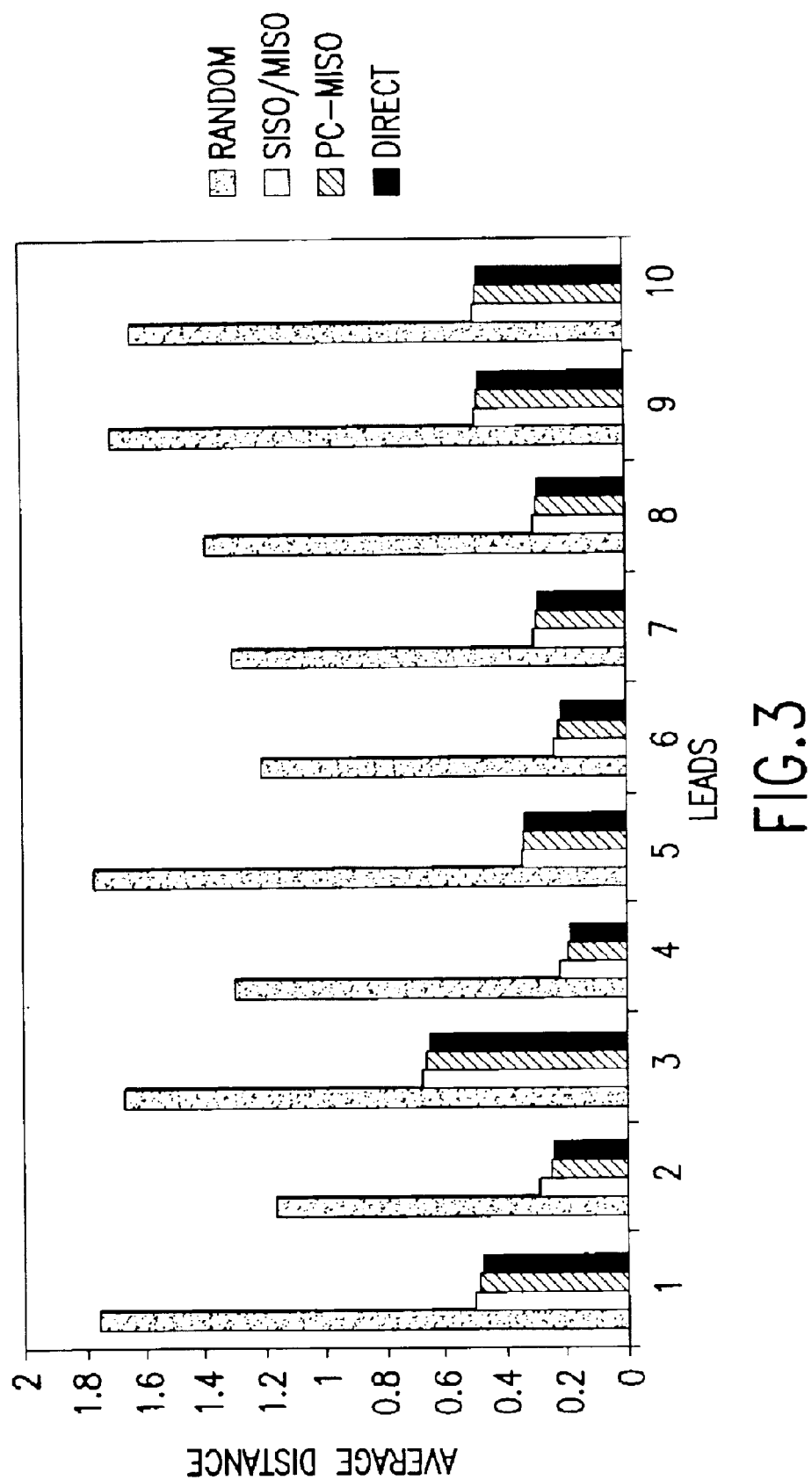
FIG. 3 illustrates average similarity scores for 10 sets of 1000 compounds most similar to each of 10 randomly chosen 'leads' as selected by various methodologies from a 6.29 million-member Ugi library according to the invention.
Figure 4A:
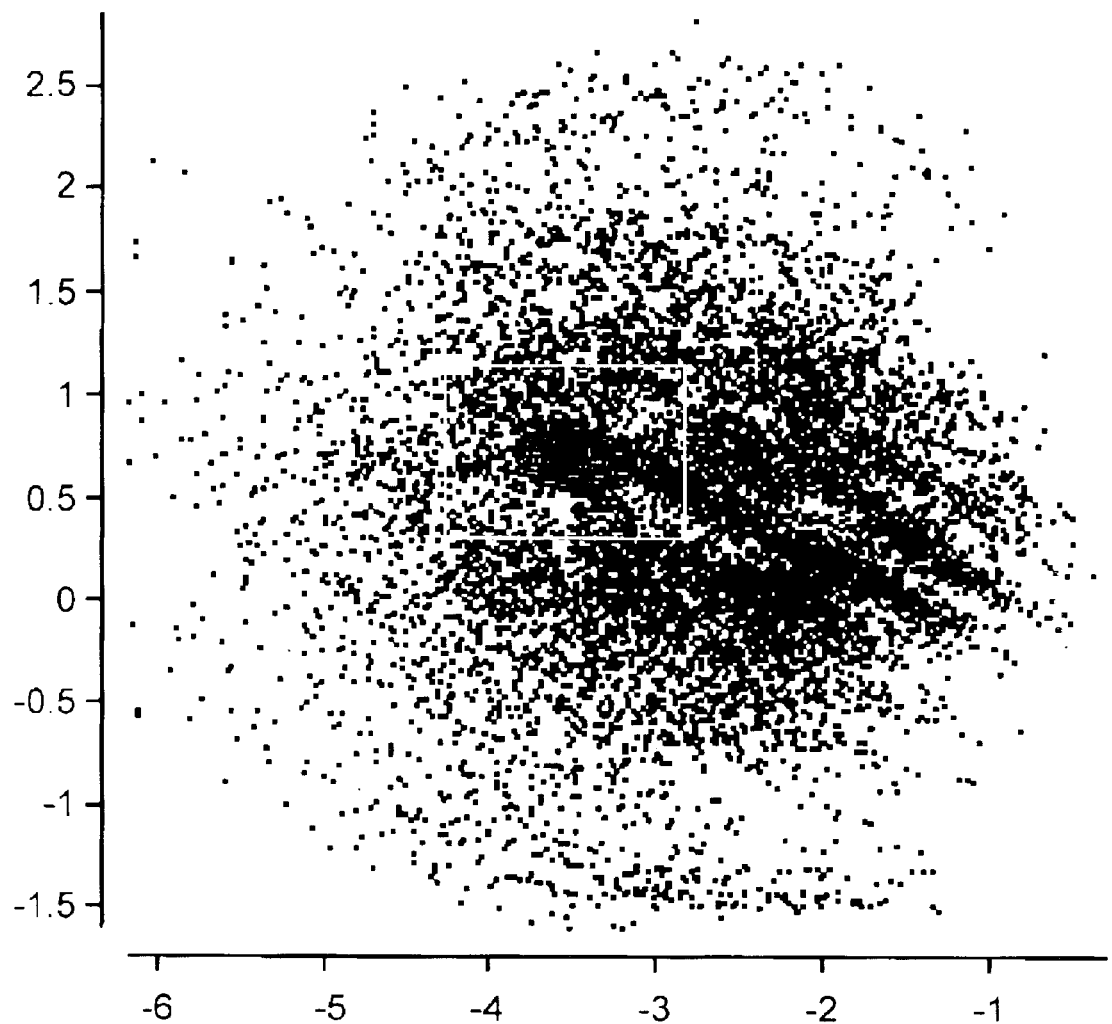
FIG. 4A illustrates a two-dimensional nonlinear map of compounds selected based on maximum similarity to a randomly chosen 'lead' using calculated product properties.
Figure 4B:
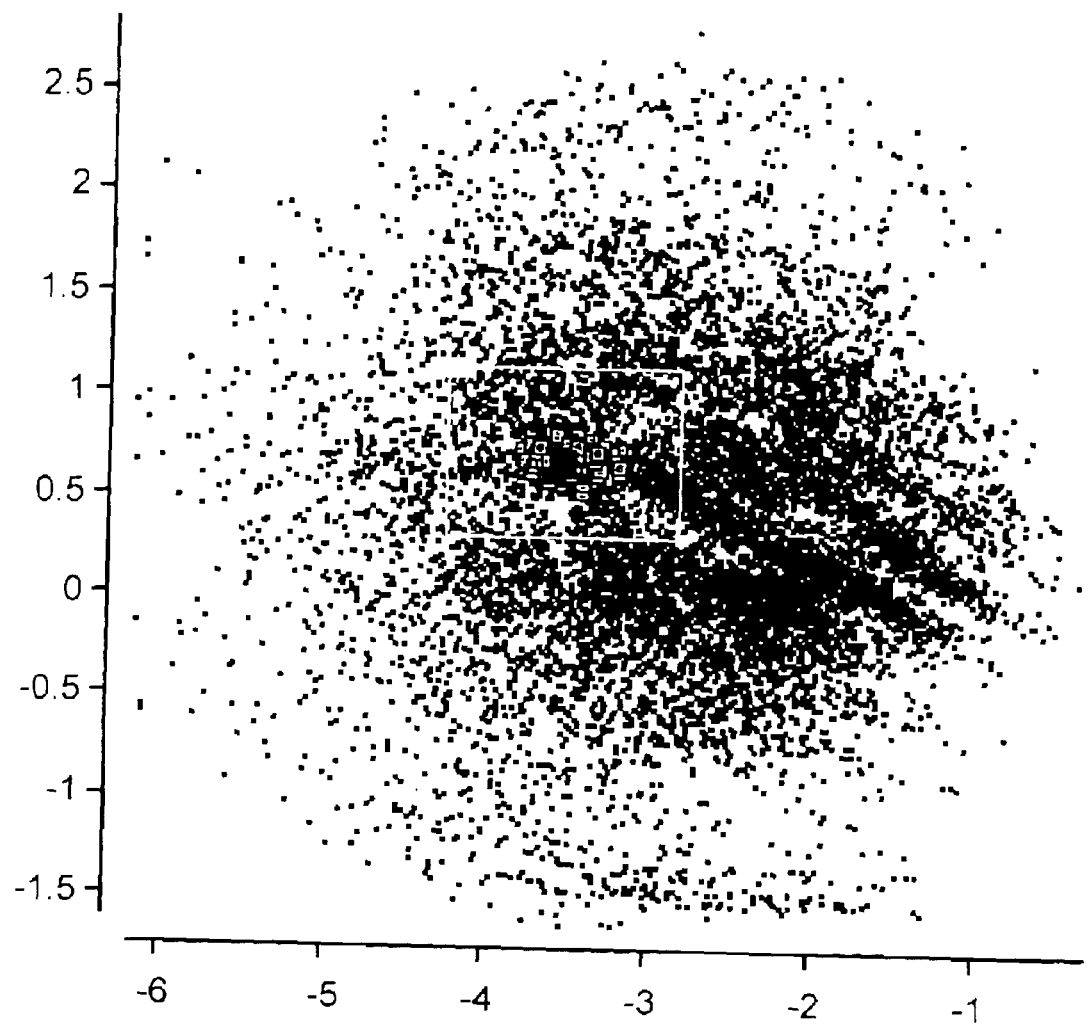
FIG. 4B illustrates a two-dimensional nonlinear map of compounds selected based on maximum similarity to a randomly chosen 'lead' using estimated product properties according to the invention.
Figure 4C:
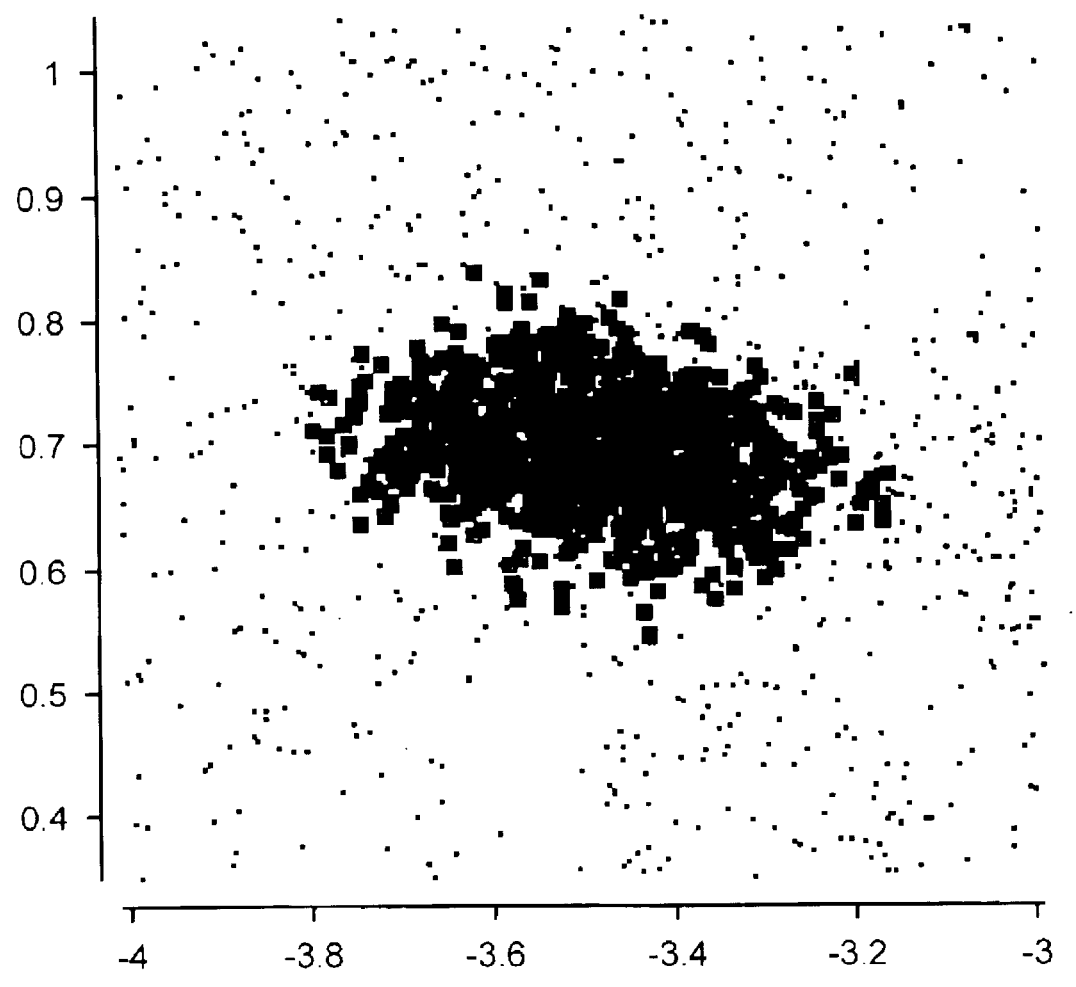
FIG. 4C illustrates a magnified view of the area outlined in FIG. 4A.
Figure 4D:
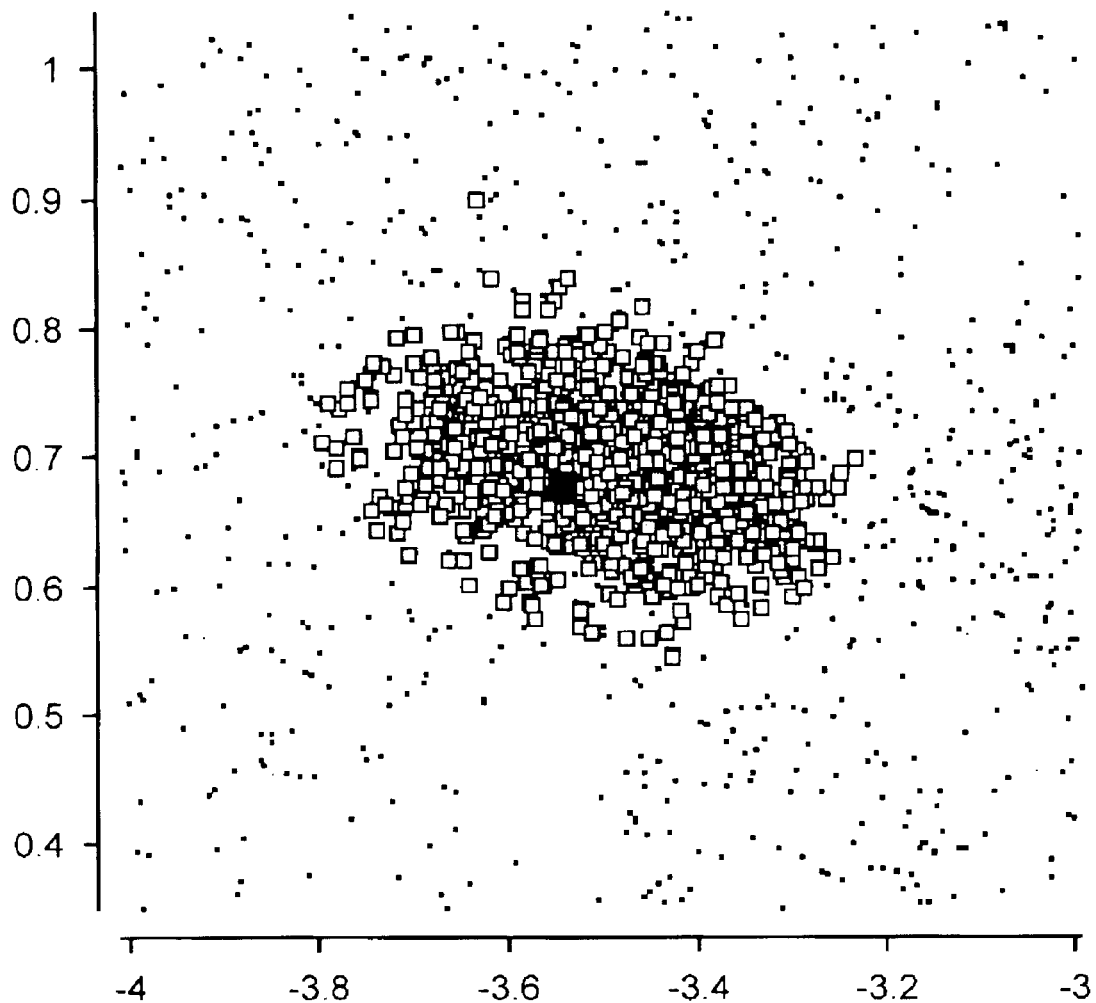
FIG. 4D illustrates a magnified view of the area outlined in FIG. 4B.

Note that in order to permit a direct comparison, the hit lists obtained with the estimated descriptors were fully enumerated, and their similarity scores were re-evaluated using calculated descriptors computed in the conventional manner. As shown in FIG. 3, in all 10 cases, the two designs had nearly identical scores and very similar content with an overlap ranging from 75 to 86 percent (see FIG. 10). The equivalence of these selections for one of the leads is graphically illustrated in the nonlinear maps of FIGS. 4A–4D. FIGS. 4A and 4C illustrate the case for the calculated descriptors. FIGS. 4B and 4D illustrate the case for the estimated descriptors. FIGS. 4C and 4D are magnified views of the areas outlined in FIGS. 4A and 4B.

Figure 6:
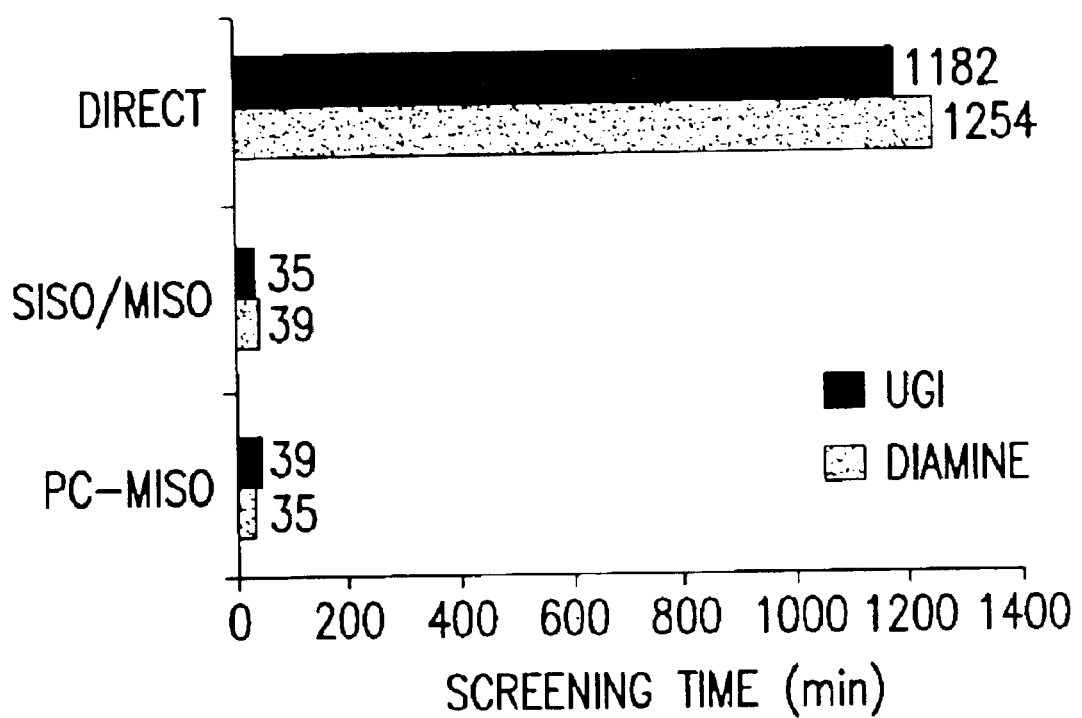
FIG. 6 illustrates a comparison of central processing unit times required for similarity searching using a conventional methodology and combinatorial neural network methodologies according to the invention.

The entire screening process, including enumeration of the training set, network training, decorrelation, and similarity searching, required only 35 minutes of CPU time. As illustrated in FIG. 6, this represents a 30-fold improvement in throughput compared to the direct approach.

Since principal components are often the desired output, significant improvements can be achieved if the evaluation of the individual descriptors are circumvented, and the combinatorial networks are trained to predict the principal components directly. As note herein, high-dimensional data sets are almost always redundant. For example, the 117 topological descriptors illustrated in FIGS. 9A–9E can be reduced to 25–30 latent variables without any significant loss in the contribution to variation. The presence of correlated variables affects molecular similarity in two important ways: (1) redundant features are effectively taken into account with a higher weight, and (2) there is a substantial and unnecessary increase in the computational effort required for data analysis.

The invention was evaluated using the combinatorial libraries described herein as follow. A sample set of 10,000 compounds was selected at random from the entire Ugi library, and was characterized using the set of 117 topological descriptors listed in FIGS. 9A–9E. These descriptors were normalized and decorrelated to 25 principal components, which accounted for 99% of the total variance in the data. In addition, all the reagents involved in making the entire Ugi library were described by the same set of descriptors, and were independently normalized and decorrelated to 27 principal components using the same variance cutoff.

These data were used to develop an array of 25 CNNs (denoted PC-MISO), each of which was trained to predict one of the product PCs using all 27 PCs from each of the 4 input reagents. Thus, each neural network was comprised of 108 input, 2 hidden, and 1 output neurons. Experiments showed that increasing the number of hidden neurons beyond two did not offer any significant improvements in the predictive ability of the resulting networks.

A set of 10,000 input-output pairs was randomly split into a training set containing 90% of the samples and a test set containing the remaining 10% of the samples. Each neural network was trained on the training set for 100 epochs or until a predefined error threshold was met. Once training was complete, the combinatorial networks were used in a feed-forward manner to predict the 25 PCs for all 6.29 million compounds in the Ugi library, which were, in turn, used to identify the 1000 most similar compounds to each of the 10 'leads' described herein.

The obtained selections were finally assessed using 'calculated' PCs and compared with the ideal solutions (see FIG. 10). Again, in all 10 cases, the selections were very similar to those derived with 'calculated' descriptors and slightly better than those derived with regular SISO and MISO CNNs, both in terms of their similarity scores and the identity of the selected compounds which ranged from 80–85% (see FIG. 10).

The entire screening process required only 39 minutes on an 800 MHz Pentium III processor.

In order to validate the generality of the invention, similar types of selections were carried out from a 3-component diamine library (see FIG. 12), using the same set of 117 topological descriptors for both reagents and products. In this case, 29 and 28 PCs were necessary to capture 99% of the variance in the reagent and products descriptors, respectively. Thus, 3-3-1 SISO and 9-3-1 MISO networks were used to predict individual descriptors, and 87-3-1 PC-MISO networks were employed for the prediction of principal components.

Figure 5:
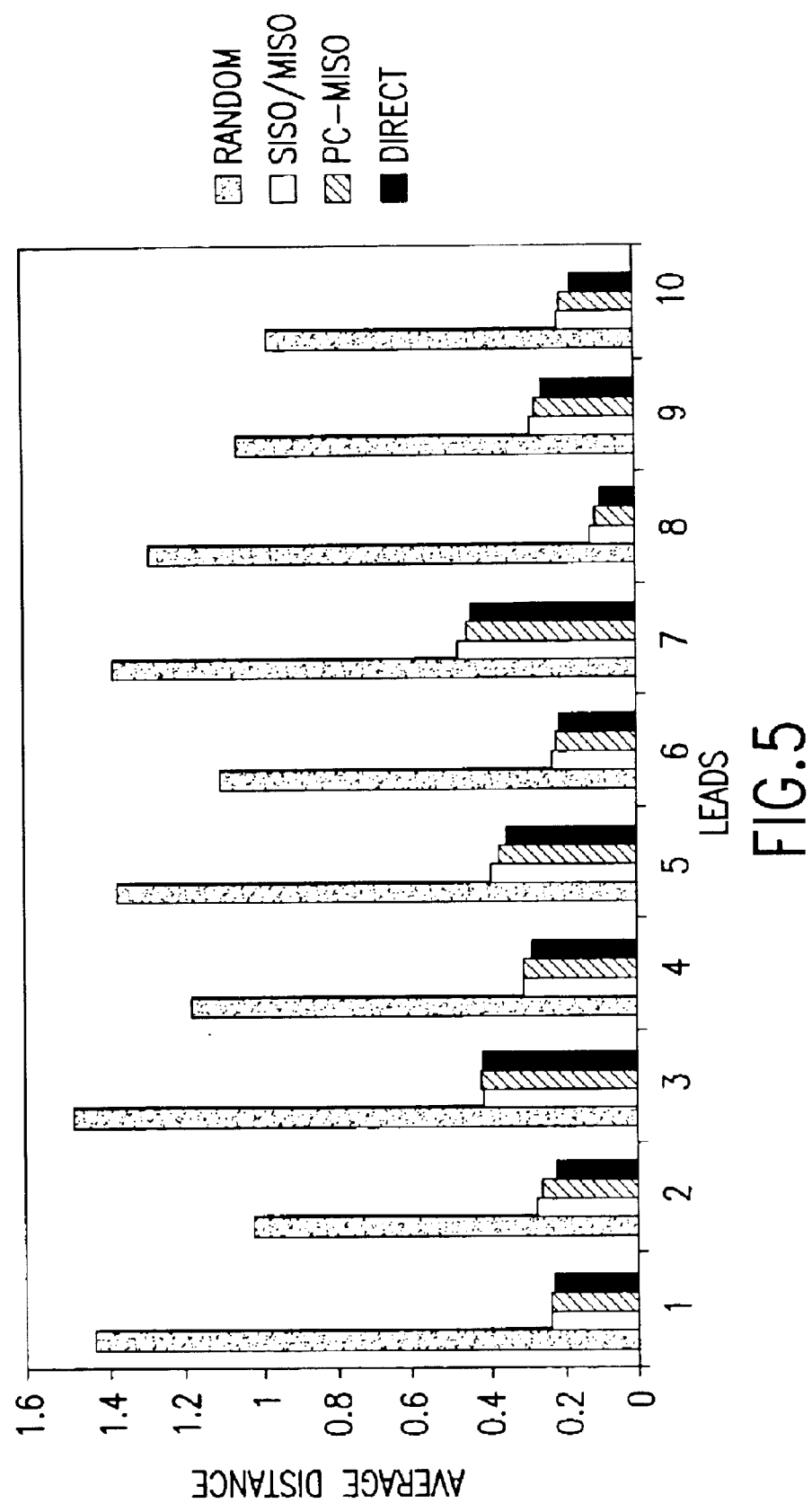
FIG. 5 illustrates average similarity scores for 10 sets of 1000 compounds most similar to each of 10 randomly chosen 'leads' as selected by various methodologies from a 6.75 million-member diamine library according to the invention.

As with the Ugi library, 10 leads were selected at random from the entire library and the 1000 most similar compounds to each of these leads were identified using the PCs derived from both the exact and approximate descriptors. Once again, the selections obtained with approximate PCs were virtually identical to the ideal solutions, with PC-MISO predictions leading to slightly better similarity scores (see FIG. 5).

The accurate reproduction of the similarity matrix is accompanied by an impressive gain in performance (see FIG. 6). Although for both libraries the training of SISO, MISO, and PC-MISO CNNs required comparable execution times, the latter performed slightly but consistently better. On the other hand, SISO and MISO networks provide access to individual descriptors, which may have additional utility in applications such as, for example, diversity profiling, ADME modeling, and structure-activity correlation. Based on the evaluations described herein, networks with multiple output nodes (i.e. multiple-input multiple-output (MIMO) perceptrons producing multiple product descriptors or principal components) tend to be more difficult to train and produced results that are less accurate than those obtained with an ensemble of single-output networks.

Figure 7:
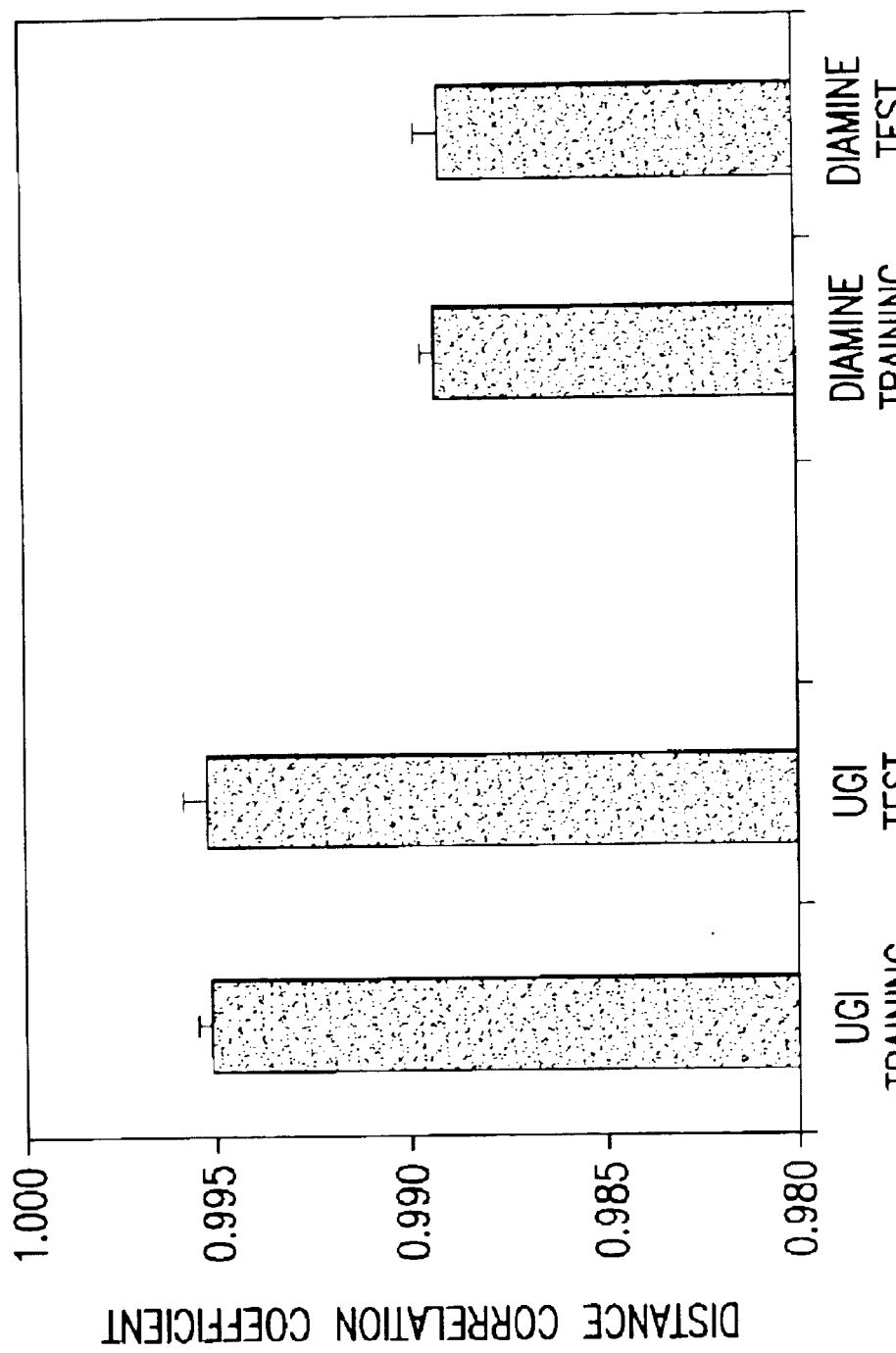
FIG. 7 illustrates the quality of estimated product properties according to the invention comparing training and test sets of products selected from two combinatorial libraries.

As described above, a common concern with any machine learning algorithm is its dependence on the nature of the training set. To examine the effect of the composition of the training set on the quality of the predictions obtained by the CNNs described herein, 10 random samples of 10,000 compounds were drawn from the Ugi library and were used to train 10 different sets of 25 PC-MISO networks. The average $R^2$ between the pairwise distances computed with 'exact' and 'approximate' PCs over all 10 trials was 0.9951±0.0004 and 0.9951±0.0006 for the training and test set, respectively. The $R^2$ was computed by comparing the Euclidean distances between 1,000,000 randomly chosen pairs of compounds in the two PC spaces. Similar standard deviations were also observed for the diamine library (0.0003 and 0.0007 for the training and test set. (See FIG. 7.) This result suggests that the training of CNNs according to the present invention is both stable and convergent.

Figure 8:
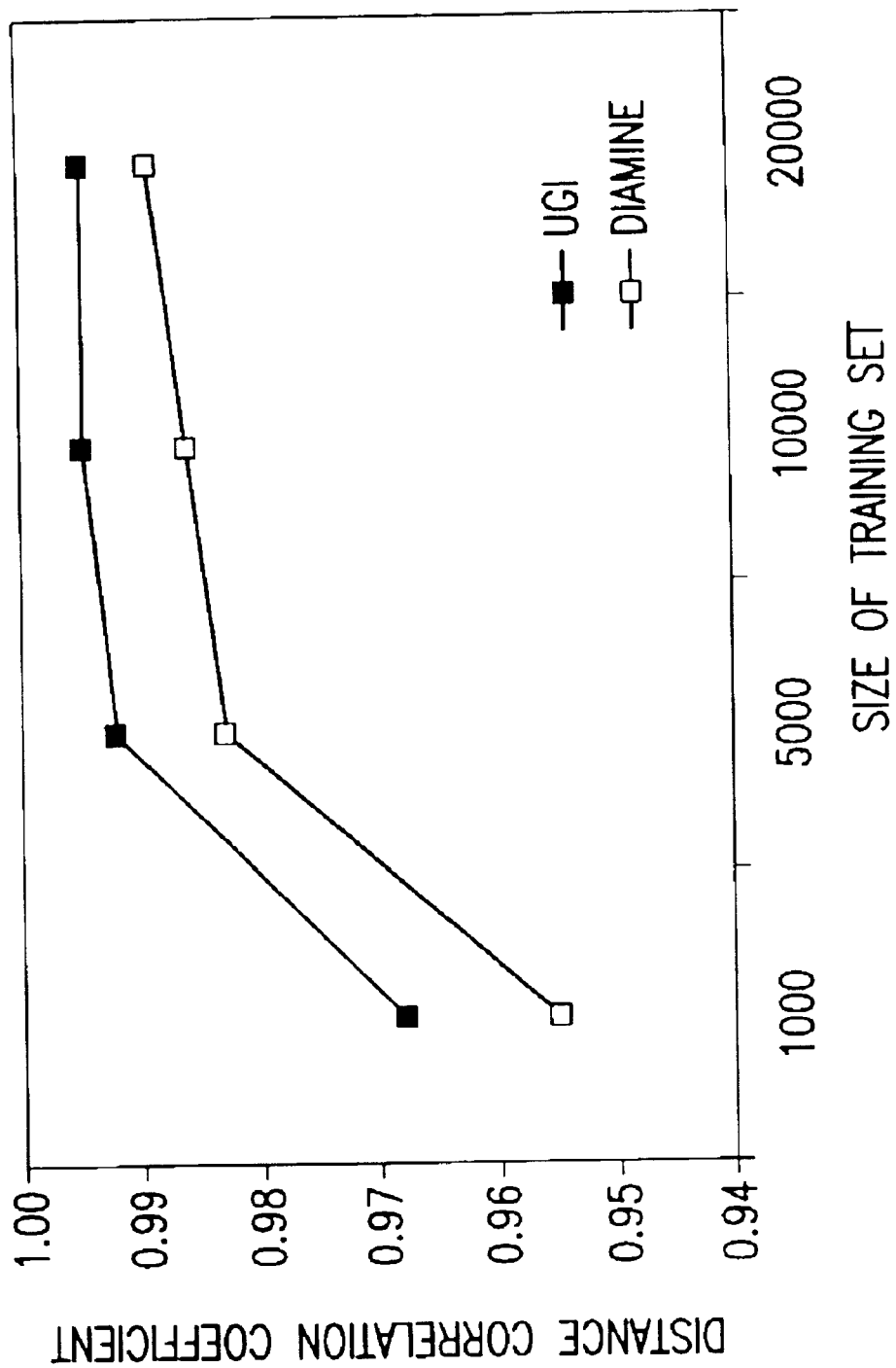
FIG. 8 illustrates the quality of estimated product properties according to the invention as a function of the training set size.

In a case of random selection, the size of the training set has a moderate effect on the quality of predictions as long as it remains large enough to sample each reagent sufficiently. The predictions improve as the size of the training set increases, and eventually plateaus after a few thousand samples (see FIG. 8). For the Ugi library there was virtually no improvement in prediction when the size of the training set was doubled from 10,000 to 20,000 compounds, but this was not the case for the diamine library where the difference in $R^2$ was still noticeable. The reason for this result is almost certainly related to the difference in the number of reagents involved in the construction of these libraries (254 for the Ugi and 400 for the diamine library) and the fact that, for a given sample size, each individual reagent is more extensively sampled in the Ugi library. The disadvantage of using larger training sets is that longer times are required for descriptor calculation and network training. Thus, in general, the sample size should be determined by weighing the benefits of higher accuracy against the increasing cost of computation.

Combinatorial Libraries

In this section, the two example Ugi and diamine combinatorial libraries used to evaluate the invention are described.

Figure 11:
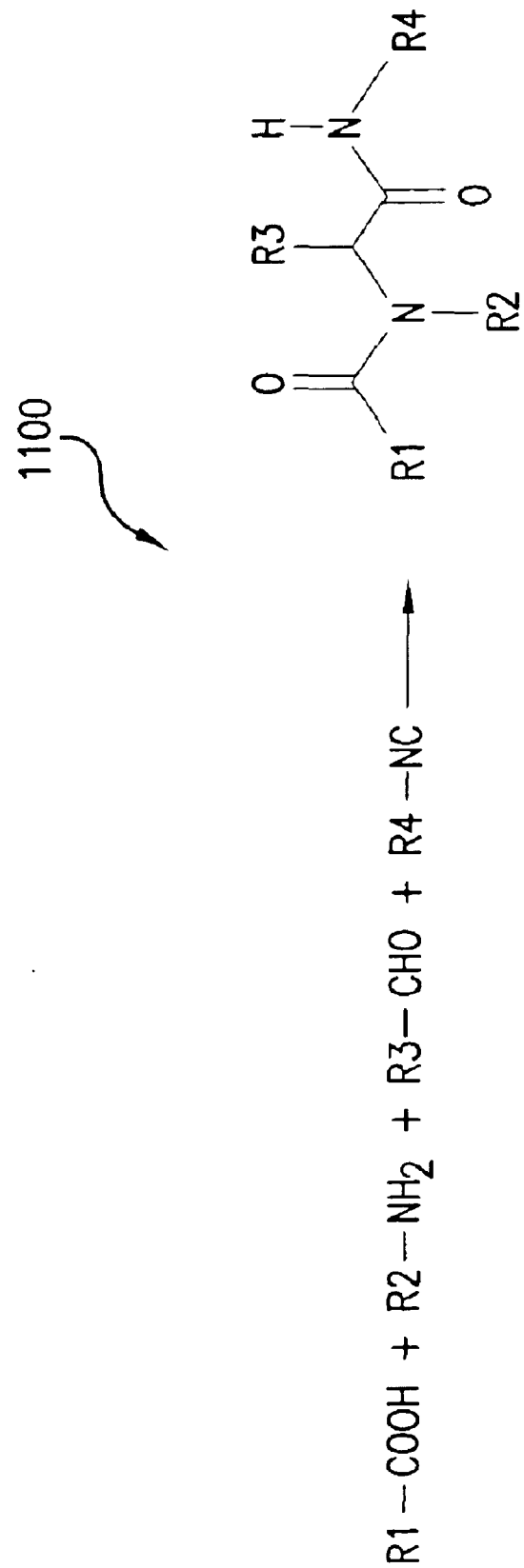
FIG. 11 illustrates a reaction scheme for a 4-component combinatorial library based on the Ugi reaction.

The first combinatorial library used to evaluate the invention was a Ugi library containing 6.29 million compounds. FIG. 11 illustrates a reaction scheme 1100 for generating a 4-component combinatorial library based on the Ugi reaction. The Ugi library used to evaluate the invention was constructed using a set of 100 acids, 100 amines, 37 aldehydes, and 17 isonitriles chosen at random from the Available Chemicals Directory (MDL Information Systems, Inc., 140 Catalina Street, San Leandro, Calif. 94577).

Figure 12:
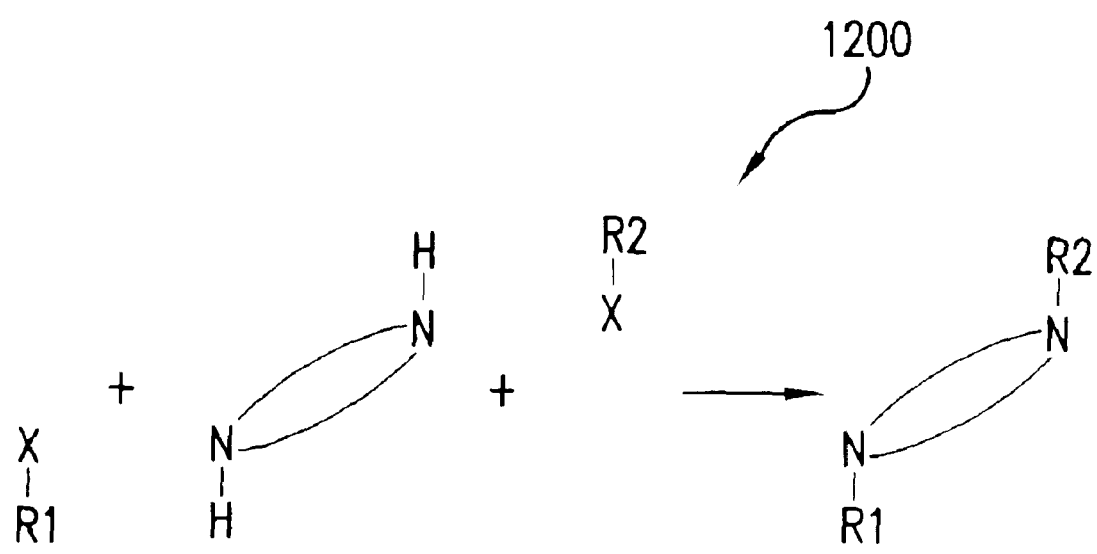
FIG. 12 illustrates a reaction scheme for a 3-component combinatorial library based on a two-step reductive amination reaction involving a diamine core and two sets of alkylating/acylating agents.

The second combinatorial library used to evaluate the invention was a diamine library containing 6.75 million compounds. FIG. 12 illustrates a reaction scheme 1200 for a combinatorial library based on a two-step reductive amination reaction involving a diamine core and two sets of alkylating/acylating agents. The diamine library used to evaluate the invention was constructed using a set of 300 diamines and two sets of 150 alkylating/acylating agents selected at random from the Available Chemicals Directory.

The size of Ugi and diamine libraries was intentionally restricted so that an exhaustive search of these libraries would be possible in order to validate the results obtained using the method embodiment of the invention described herein. Both the reagents and the products of these libraries were characterized by a set of 117 topological descriptors, including molecular connectivity indices, kappa shape indices, subgraph counts, information-theoretic indices, Bonchev-Trinajstis indices, and topological state indices. These descriptors have a proven track record in structure-activity analysis, can be computed directly from the connection table, and are consistent with the medicinal chemists' perception of molecular similarity. Moreover, they have been shown to exhibit proper 'neighborhood behavior' and are thus well suited for diversity analysis and similarity searching. These data were subsequently normalized and decorrelated using principal component analysis (PCA), resulting in an orthogonal set of 25 to 29 latent variables, which accounted for 99% of the total variance in the data. The PCA preprocessing step was necessary in order to eliminate duplication and redundancy in the data, which is typical of graph-theoretic descriptors.

For the nonlinear maps illustrated in FIGS. 4A–D, this multidimensional data was further reduced to two dimensions using the methodology described in U.S. patent application Ser. No. 09/823,977, filed Apr. 3, 2001, titled "Method, System, And Computer Program Product For Representing Object Relationships In A Multidimensional Space," which is incorporated by reference herein in its entirety. The pair-wise distances between the points in the multidimensional principle component space are preserved on the two-dimensional nonlinear maps of FIGS. 4A–D. The two-dimensional nonlinear maps of FIGS. 4A–D were used to visualize the product selections described herein, which were carried out using all significant principle components.

Summary

As described above, the method of the invention can be used to estimate or predict properties of products using the features of reagents, thereby effectively eliminating the need to enumerate and describe every individual product in a virtual combinatorial chemical library. By circumventing enumeration and replacing descriptor evaluation with a simple feed-forward pass through a combinatorial neural network according to the invention, the invention permits the in silico characterization and screening of huge combinatorial libraries unmanageable by other means. Although the descriptors or properties produced by the invention are estimated values rather than calculated values, any differences between the estimated values of the invention and the calculated values obtained using conventional methods is minimal and has little or no impact on similarity searching. Embodiments of the invention are more than an order of magnitude faster than conventional enumerative similarity searching methodologies, and this differential increases with the size and combinatorial complexity of the virtual library under investigation.

System and Computer Program Product Embodiments

Figure 13:
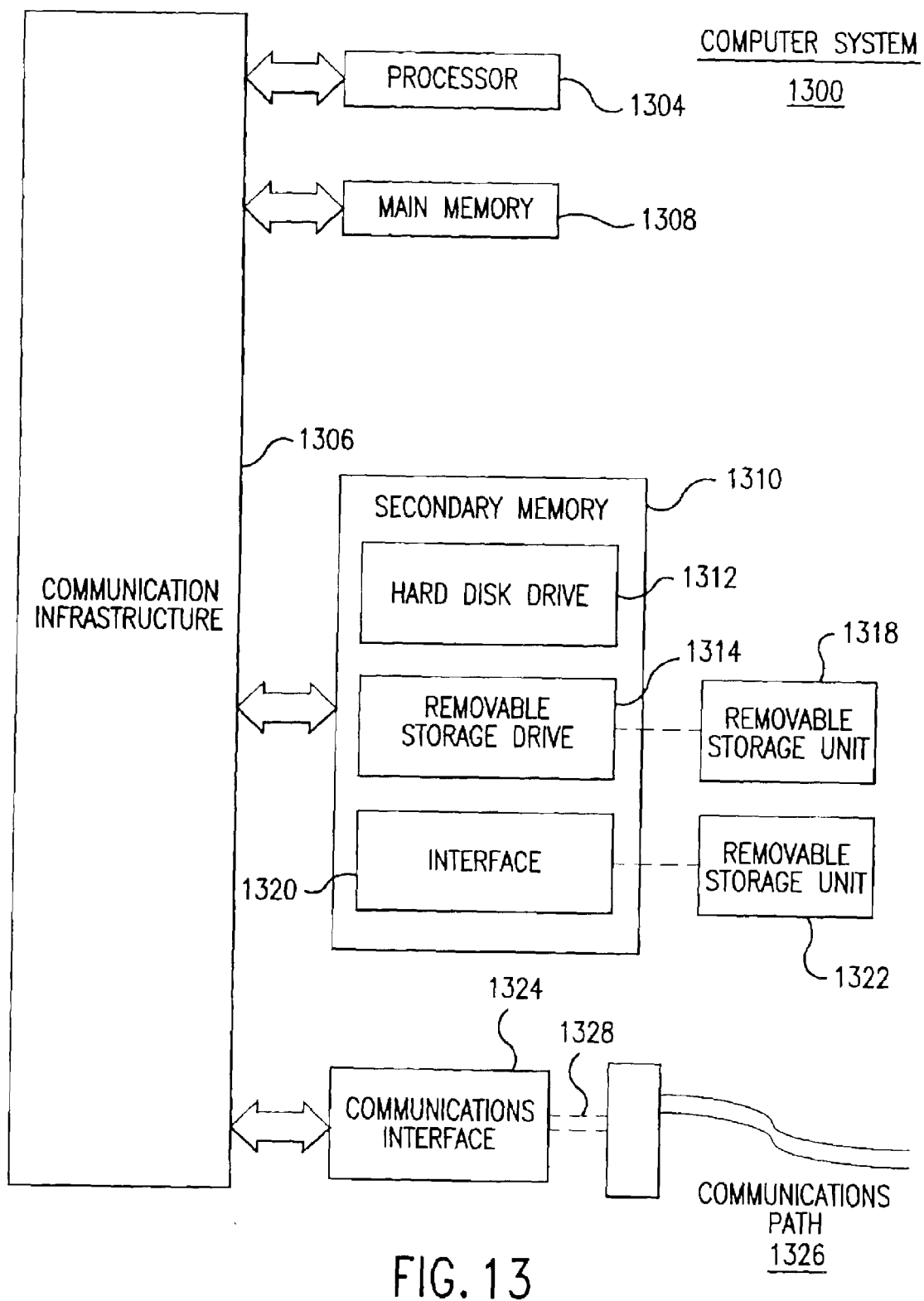
FIG. 13 illustrates an exemplary computing environment within which the invention can operate.

As will be understood by a person skilled in the relevant arts given the description herein, the method embodiment of the invention described above can be implemented as a system and/or a computer program product. FIG. 13 shows an example computer system 1300 that supports implementation of the present invention. The present invention may be implemented using hardware, software, firmware, or a combination thereof. It may be implemented in a computer system or other processing system. The computer system 1300 includes one or more processors, such as processor 1304. The processor 1304 is connected to a communication infrastructure 1306 (e.g., a bus or network). Various software embodiments can be described in terms of this exemplary computer system. After reading this description, it will become apparent to a person skilled in the relevant art how to implement the invention using other computer systems and/or computer architectures.

Computer system 1300 also includes a main memory 1308, preferably random access memory (RAM), and may also include a secondary memory 1310. The secondary memory 1310 may include, for example, a hard disk drive 1312 and/or a removable storage drive 1314, representing a floppy disk drive, a magnetic tape drive, an optical disk drive, etc. The removable storage drive 1314 reads from and/or writes to a removable storage unit 1318 in a well-known manner. Removable storage unit 1318 represents a floppy disk, magnetic tape, optical disk, etc. As will be appreciated, the removable storage unit 1318 includes a computer usable storage medium having stored therein computer software and/or data. In an embodiment of the invention, removable storage unit 1318 can contain input data to be projected.

Secondary memory 1310 can also include other similar means for allowing computer programs or input data to be loaded into computer system 1300. Such means may include, for example, a removable storage unit 1322 and an interface 1320. Examples of such may include a program cartridge and cartridge interface (such as that found in video game devices), a removable memory chip (such as an EPROM, or PROM) and associated socket, and other removable storage units 1322 and interfaces 1320, which allow software and data to be transferred from the removable storage unit 1322 to computer system 1300.

Computer system 1300 may also include a communications interface 1324. Communications interface 1324 allows software and data to be transferred between computer system 1300 and external devices. Examples of communications interface 1324 may include a modem, a network interface (such as an Ethernet card), a communications port, a PCMCIA slot and card, etc. Software and data transferred via communications interface 1324 are in the form of signals 1328 which may be electronic, electromagnetic, optical or other signals capable of being received by communications interface 1324. These signals 1328 are provided to communications interface 1324 via a communications path (i.e., channel) 1326. This channel 1326 carries signals 1328 and may be implemented using wire or cable, fiber optics, a phone line, a cellular phone link, an RF link and other communications channels. In an embodiment of the invention, signals 1328 can include input data to be projected.

Computer programs (also called computer control logic) are stored in main memory 1308 and/or secondary memory 1310. Computer programs may also be received via communications interface 1324. Such computer programs, when executed, enable the computer system 1300 to perform the features of the present invention as discussed herein. In particular, the computer programs, when executed, enable the processor 1304 to perform the features of the present invention. Accordingly, such computer programs represent controllers of the computer system 1300.

Conclusion

While various embodiments of the present invention have been described above, it should be understood that they have been presented by way of example, and not limitation. It will be apparent to persons skilled in the relevant art that various changes in detail can be made therein without departing from the spirit and scope of the invention. Thus the present invention should not be limited by any of the above-described exemplary embodiments, but should be defined only in accordance with the following claims and their equivalents.

What is claimed is:

1. A method for determining properties of products from a combinatorial chemical library P using features of their respective building blocks, the method comprising the steps of:

(1) determining at least one feature for each building block in the combinatorial library P, $\{a_{ijk}, i=1,2,\ldots,r; j=1,2,\ldots,r_i; k=1,2,\ldots,n_i\}$, wherein r represents the number of variation sites in the combinatorial library, $r_i$ represents the number of building blocks at the i-th variation site, and $n_i$ represents the number of features used to characterize each building block at the i-th variation site;

(2) selecting a training subset of products $\{p_i, i=1,2,\ldots,m; p_i \in P\}$ from the combinatorial library P;

(3) determining q properties for each compound $p_i$ in the selected training subset of products, wherein $y_i$ $\{y_{ij}, i=1,2,\ldots,m, j=1,2,\ldots,q\}$ represents the determined properties of compound $p_i$, and wherein q is greater or equal to one;

(4) identifying, for each product $p_i$ of the training subset of products, the corresponding building blocks $\{t_{ij}, t_{ij}=1,2,\ldots,r_j, j=1,2,\ldots,r\}$ and concatenating their features determined in step (1) into a single vector $\{x_i = a_{1t_{i1}} | a_{2t_{i2}} | a_{rt_{ir}}\}$;

(5) using a supervised machine learning approach to infer a mapping function $f$ that transforms input values $x_i$, to output values $y_i$, from the input/output pairs in the training set $T=\{(x_i, y_i), i=1,2,\ldots,m\}$;

(6) identifying, after the mapping function $f$ is determined, for a product $p_z \in P$, the corresponding building blocks $\{t_{zj}, j=1,2,\ldots,r\}$ and concatenating their features, $a_{1t_{z1}}, a_{2t_{z1}}, \ldots, a_{rt_{zr}}$, into a single vector $\{x_z = a_{1t_{z1}} | a_{2t_{z2}} | \ldots | a_{rt_r}\}$, and (7) mapping $x_z \rightarrow y_z$, using the mapping function $f$ determined in step (5), wherein $y_z$ represents the properties of product $p_z$.

2. The method of claim 1, wherein step (1) comprises the step of:
   using a measured value as a feature for each building block.

3. The method of claim 1, wherein step (1) comprises the step of:
   using a computed value as a feature for each building block.

4. The method of claim 1, wherein step (3) comprises the step of:
   using a measured value as a property for each product of the training subset.

5. The method of claim 1, wherein step (3) comprises the step of:
   using a computed value as a property for each product of the training subset.

6. The method of claim 1, wherein step (5) comprises the step of:
   training a multilayer perceptron.

7. The method of claim 1, wherein
   at least one of the features determined in step (1) is the same as at least one of the properties determined in step (3).

8. The method of claim 1, wherein
   the building blocks comprise a plurality of reagents used to construct the combinatorial library P.

9. The method of claim 1, wherein
   the building blocks comprise a plurality of fragments of a plurality of reagents used to construct the combinatorial library P.

10. The method of claim 1, wherein
    the building blocks comprise a plurality of modified fragments of a plurality of reagents used to construct the combinatorial library P.

11. The method of claim 1, wherein step (2) comprises the step of:
    selecting a training subset of products at random.

12. The method of claim 1, wherein step (2) comprises the step of:
    selecting a training subset of products using a combinatorial design method to cover all pairwise combinations of building blocks.

13. The method of claim 1, wherein step (2) comprises the step of:
    selecting a training subset of products using a diversity metric to select a diverse subset of products.

* * * * *

UNITED STATES PATENT AND TRADEMARK OFFICE
CERTIFICATE OF CORRECTION

PATENT NO. : 6,834,239 B2  
APPLICATION NO. : 09/934084  
DATED : December 21, 2004  
INVENTOR(S) : Lobanov et al.

Page 1 of 1

It is certified that error appears in the above-identified patent and that said Letters Patent is hereby corrected as shown below:

In the claims, at column 15, line 63, claim 1:

" $\{x_i = a_{1t_{i1}} | a_{2t_{i2}} | a_{rt_{ir}}\}$ " should read -- $\{x_i = a_{1t_{i1}} | a_{2t_{i2}} | a_{rt_{ir}}\}$ --

In the claims, at column 16, line 8, claim 1:

" their features, $a_{1t_{z1}}, a_{2t_{21}}, ..., a_{rt_{zr}}$ " should read -- their features, $a_{1t_{z1}}, a_{2t_{21}}, ..., a_{rt_{zr}},$ --

Signed and Sealed this

Twenty-fourth Day of October, 2006

JON W. DUDAS  
*Director of the United States Patent and Trademark Office*